(12) United States Patent
Koyakutty et al.

(10) Patent No.: US 11,369,681 B2
(45) Date of Patent: Jun. 28, 2022

(54) RADIO-WAVE RESPONSIVE DOPED NANOPARTICLES FOR IMAGE-GUIDED THERAPEUTICS

(71) Applicant: Amrita Vishwa Vidyapeetham, Kochi (IN)

(72) Inventors: Manzoor Koyakutty, Kochi (IN); Anusha Ashokan, Kochi (IN); Vijay Harish, Kochi (IN); Shantikumar Nair, Kochi (IN)

(73) Assignee: Amrita Vishwa Vidyapeetham, Kochi (IN)

( * ) Notice: Subject to any disclaimer, the term of this patent is extended or adjusted under 35 U.S.C. 154(b) by 61 days.

(21) Appl. No.: 15/780,654

(22) PCT Filed: Dec. 5, 2016

(86) PCT No.: PCT/US2016/064890
§ 371 (c)(1),
(2) Date: Jun. 1, 2018

(87) PCT Pub. No.: WO2017/096342
PCT Pub. Date: Jun. 8, 2017

(65) Prior Publication Data
US 2019/0000973 A1  Jan. 3, 2019

(30) Foreign Application Priority Data
Dec. 3, 2015 (IN) .......................... 6495/CHE/2015

(51) Int. Cl.
| A61K 41/00 | (2020.01) |
| A61K 49/18 | (2006.01) |
| A61K 9/00  | (2006.01) |
| A61B 18/14 | (2006.01) |
| B82Y 5/00  | (2011.01) |

(52) U.S. Cl.
CPC .......... *A61K 41/0052* (2013.01); *A61B 18/14* (2013.01); *A61K 9/0024* (2013.01); *A61K 49/1818* (2013.01); *B82Y 5/00* (2013.01)

(58) Field of Classification Search
None
See application file for complete search history.

(56) References Cited

U.S. PATENT DOCUMENTS

| 5,342,609 A | 8/1994 | Meeh et al. |
| 5,690,908 A | 11/1997 | Deutsch et al. |
| 2004/0166172 A1 | 8/2004 | Rosati et al. |
| 2010/0092364 A1 | 4/2010 | Kasinath et al. |
| 2011/0182805 A1 | 7/2011 | Desimone et al. |
| 2011/0318422 A1 | 12/2011 | Kuhn et al. |
| 2012/0184642 A1 | 7/2012 | Bartling et al. |
| 2012/0201872 A1 | 8/2012 | Huang et al. |
| 2014/0044643 A1 | 2/2014 | Cheng et al. |
| 2015/0265725 A1 | 9/2015 | Peyman et al. |

FOREIGN PATENT DOCUMENTS

| EP | 2198885 B1 | 2/2012 |
| WO | 2011057216 A1 | 5/2011 |
| WO | 2011151631 A1 | 12/2011 |
| WO | 2014110449 A1 | 7/2014 |
| WO | 2014141287 A1 | 9/2014 |
| WO | 2014141288 A1 | 9/2014 |

OTHER PUBLICATIONS

Ashokan et al. Multifunctional calcium phosphate nano-contrast agent for combined nuclear, magnetic and near-infrared in vivo imaging. 2013 Biomaterials 34: 7143-7157. (Year: 2013).*
International Preliminary Report on Patentability Chapter I for Application No. PCT/US2016/064890, dated Jun. 5, 2018, 12 pages.
International Search Report and Written Opinion for Application No. PCT/US2016/064890, dated Feb. 21, 2017, 13 pages.

* cited by examiner

*Primary Examiner* — Jennifer Lamberski
(74) *Attorney, Agent, or Firm* — Hamre, Schumann, Mueller & Larson, P.C.

(57) ABSTRACT

The invention discloses nanoparticles comprising compounds of calcium with anions such as phosphate, pyrophosphate, sulphate, silicate, carbonate, molybdate, or phosphosilicate that are doped with various ions. The nanoparticles are configured to produce heat (hyperthermia) under radio-wave (1 KHz-1000 GHz) exposure together with magnetism suitable for contrast imaging in MRI, X-ray absorption for computed tomography, near-infrared optical fluorescence for optical imaging, and/or radio-isotope emission for nuclear imaging or therapy. The nanoparticles can also be incorporated into micro-beads or other 3 dimensional scaffolds for image-guided (MRI, CT, NIR, nuclear) tissue regeneration, immunotherapy, vascular or tumor embolization, and/or chemo/radio-embolization.

12 Claims, 16 Drawing Sheets

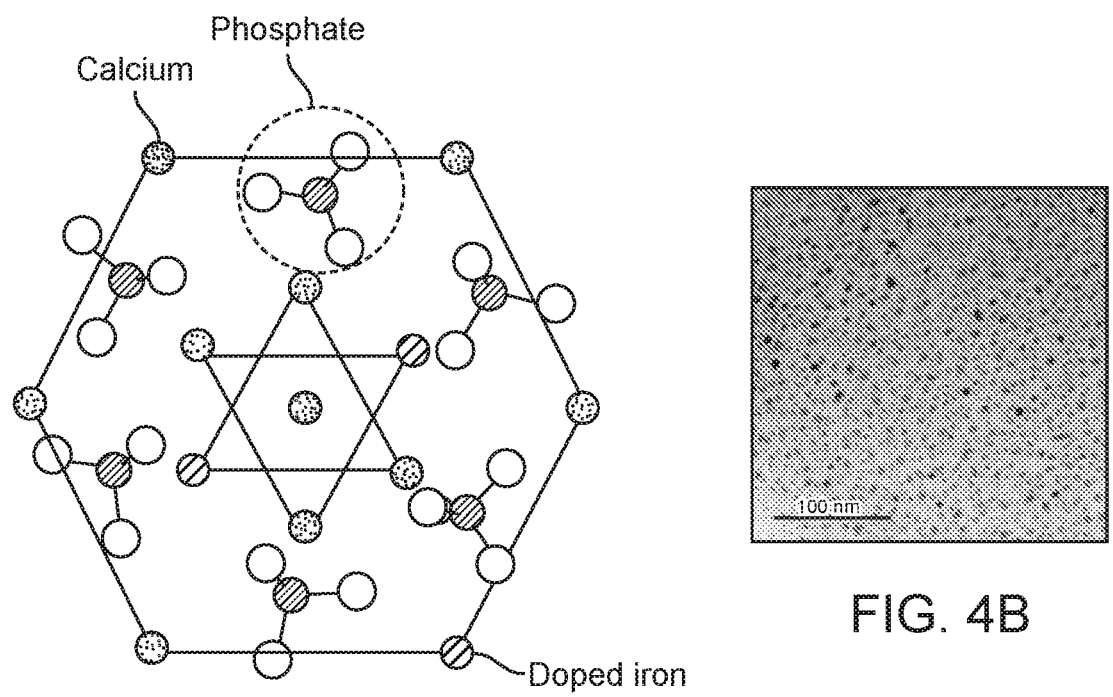
FIG. 4A
FIG. 4B
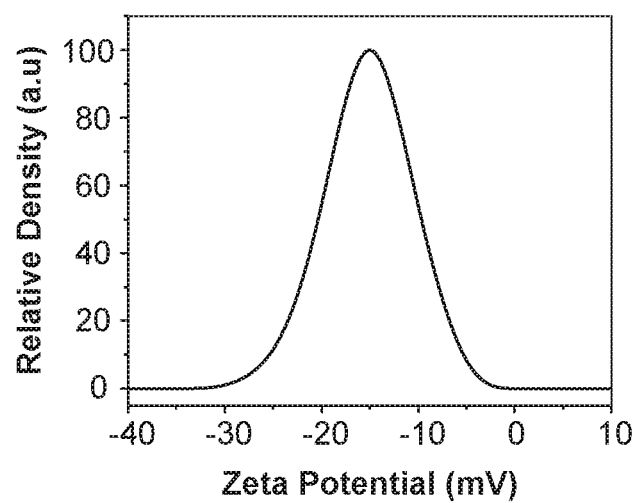
FIG. 5

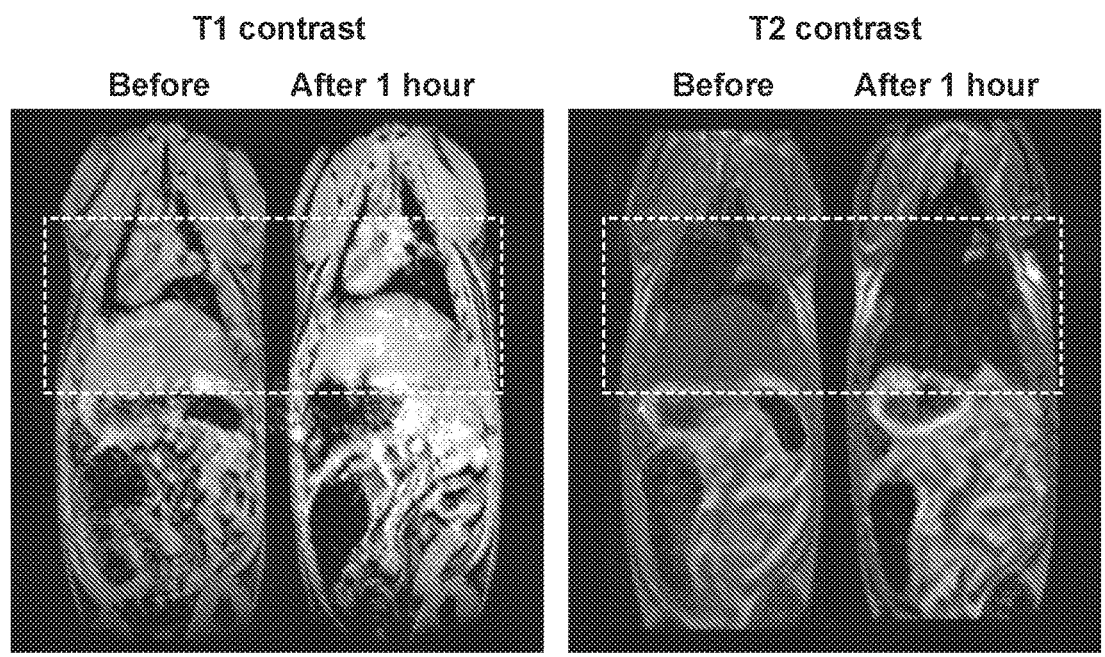
FIG. 8A   FIG. 8B
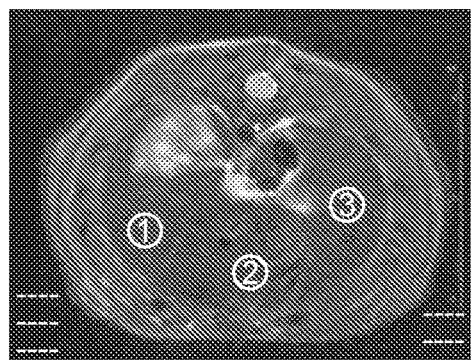   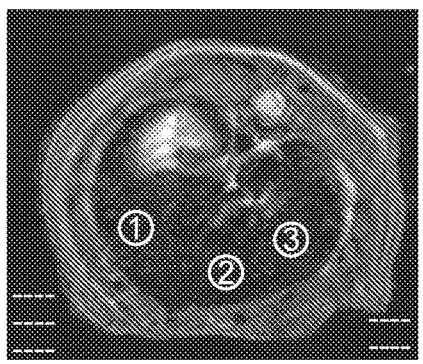
FIG. 8C   FIG. 8D
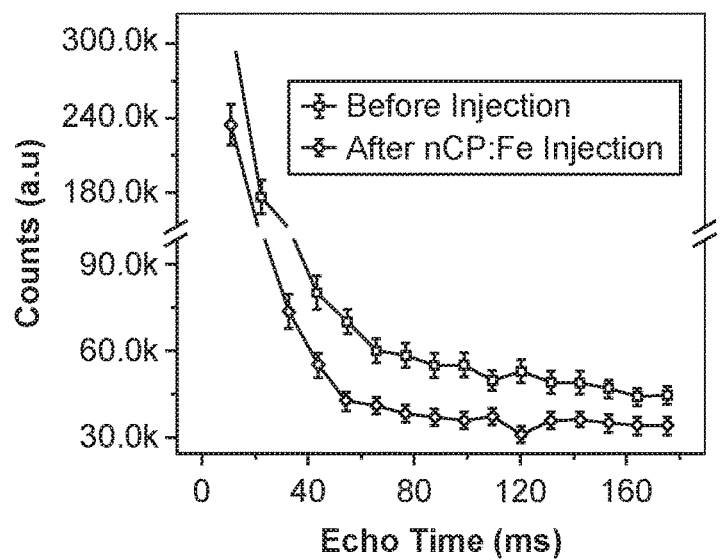
FIG. 8E

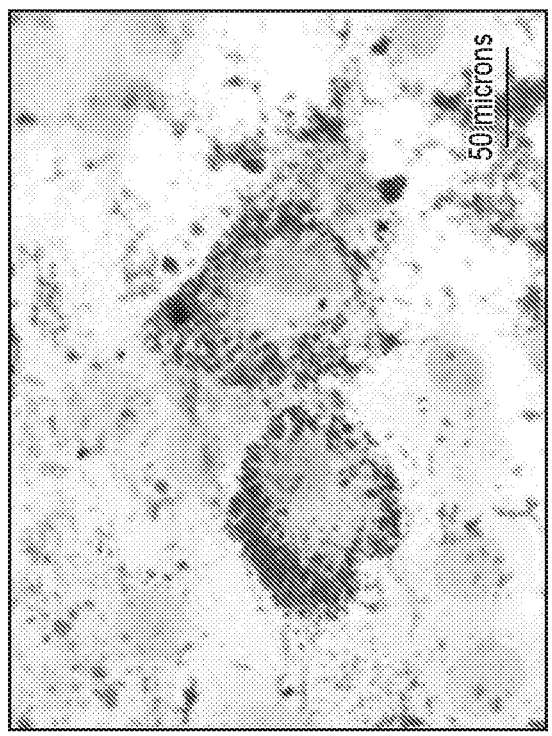
FIG. 17A
FIG. 17B
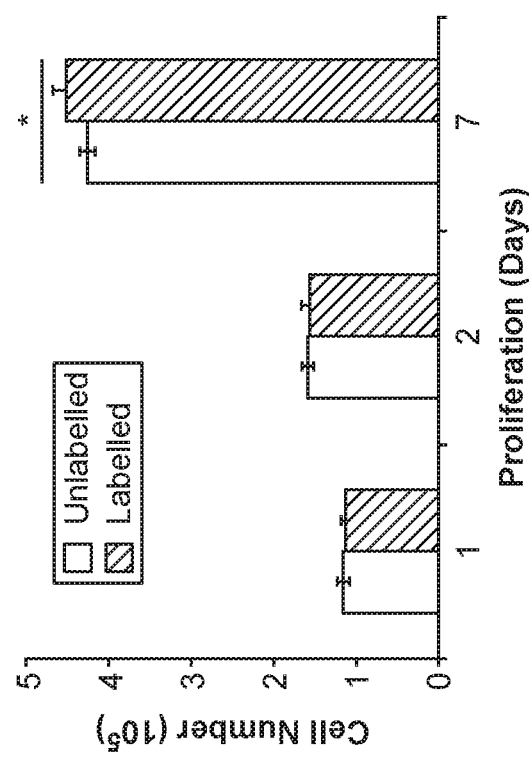
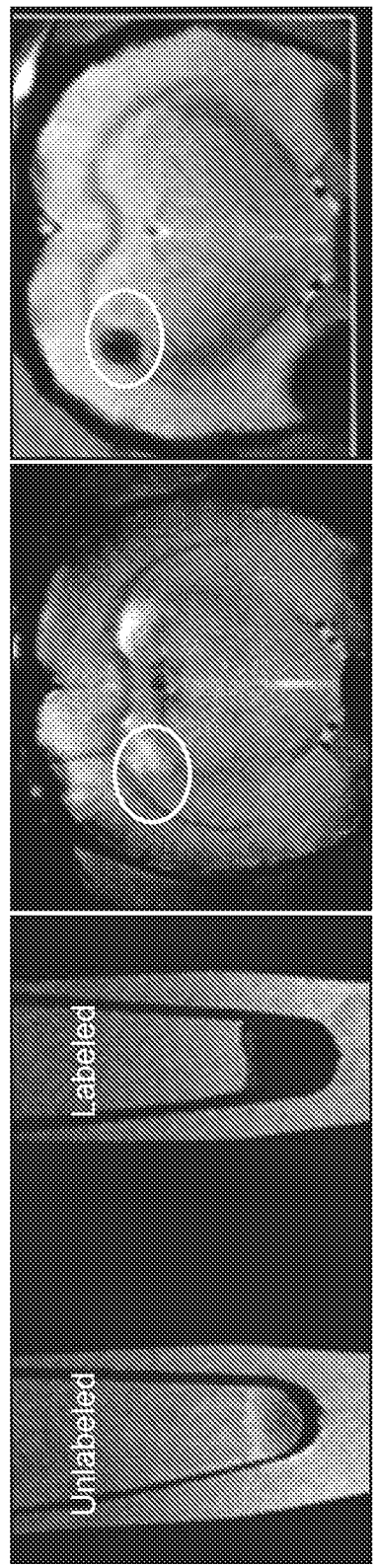
FIG. 17C
FIG. 17D
FIG. 17E

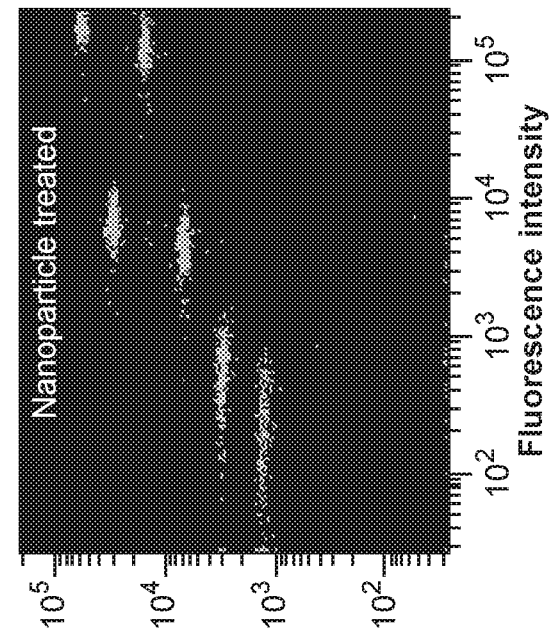
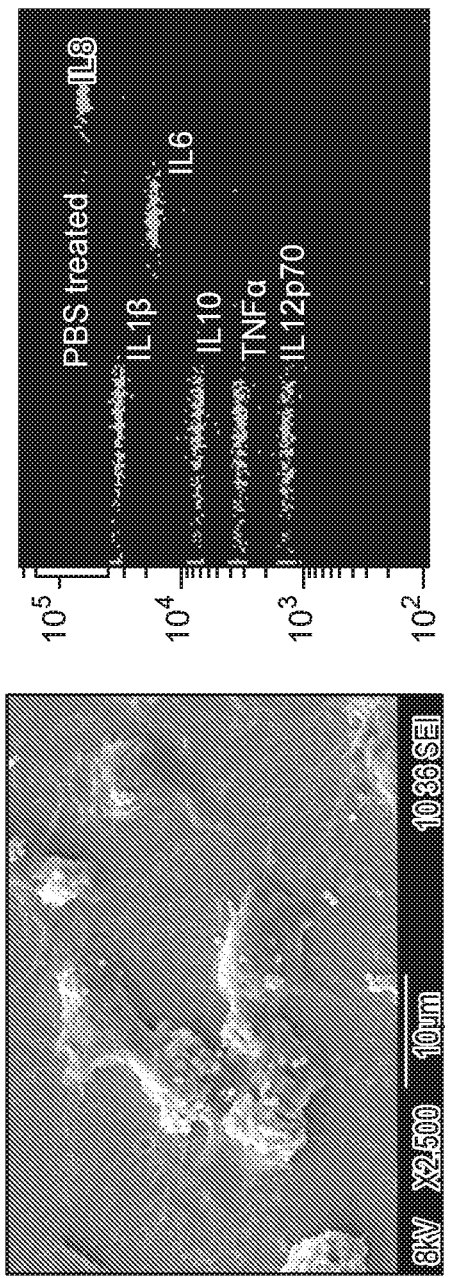
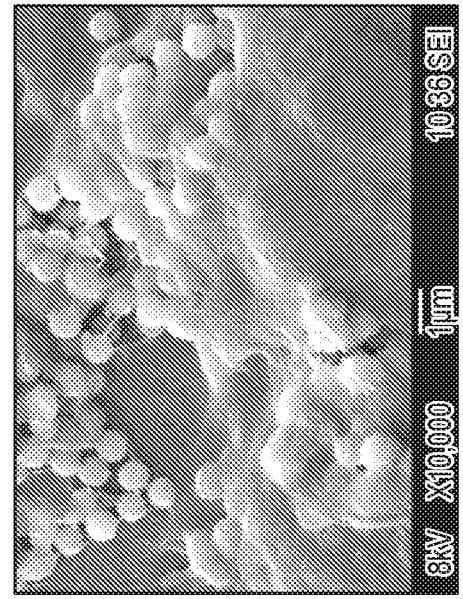
FIG. 20A
FIG. 20B
FIG. 20C
FIG. 20D

RADIO-WAVE RESPONSIVE DOPED NANOPARTICLES FOR IMAGE-GUIDED THERAPEUTICS

CROSS-REFERENCES TO RELATED APPLICATIONS

This application is the National Stage of International Application No. PCT/US2016/064890, filed on 5 Dec. 2016, which claims priority to Indian patent application No. 6495/CHE/2015, filed on 3 Dec. 2015, the full disclosure of which are incorporated herein by reference.

FIELD OF THE INVENTION

The present invention relates to image guided therapeutics and in particular to nanoparticle compositions that produce heat or hyperthermia on exposure to alternating radiofrequency waves, with simultaneous visibility under multiple imaging mechanisms.

DESCRIPTION OF THE RELATED ART

Radiofrequency ablation (RFA) is a treatment technique used in the clinics for treating tumors, cardiac problems, pain and varicose veins. It is based on the principle of hyperthermia for the destruction of diseased tissues. In clinics, RFA is administered by placing one or more electrodes in the diseased tissue and the application of alternating current or field in the radiofrequency range. Heating takes place in the tissue near to the emitting electrodes. Hyperthermia therapy refers to application of temperatures in the range of 40-50° C. while application of temperatures above 50° C. is referred to as thermo ablation. The major limitation of current RFA is that the size of the lesion that can be treated is limited to 4 cm or less. In clinics, this problem is addressed by repeated repositioning of RF electrodes in order to cover the entire disease area. Recent developments such as expandable and internally cooled electrodes have helped to increase the area of ablation to a small extent. In addition, normal saline infusion has been shown to be effective in enlarging the area of necrosis during radiofrequency ablation, by improving the conductivity 3-5 times greater than that of blood and 12-15 times greater than that of soft tissues. Currently RFA is done under ultrasound guidance that provides poor contrast for the diseased tissue. RF probe can be applied more accurately if the contrast of the diseased tissue is enhanced by MRI, CT or PET/SPECT-CT.

Calcium phosphosilicate nanoparticles have been developed for near infrared imaging and drug delivery applications (WO2011057216 A1). Calcium phosphate nanoparticles have also been disclosed for encapsulating photosensitizers for PDT (EP 2 198 885 B1) and for delivery of therapeutics to tumor cells and lymphatics for treatment of cancer and prevention of metastasis (US 2011/0318422 A1). The application of iron oxide incorporated calcium phosphate nanoparticles has been disclosed for applications such as magnetic hyperthermia, imaging, drug delivery (US 2014/0044643). A few other references discuss the development of doped apatite and calcium phosphate nanoparticles for different combinations of optical, MRI, X-ray, nuclear and/or ultrasound imaging (U.S. Pat. No. 5,342,609, U.S. Pat. No. 5,690,908, WO 2011151631 A1, US 2010/0092364 A1).

The present invention is directed at nanoparticle formulations that aid in locating lesions through visualization by various methods in combination or independently, while simultaneously providing localized ablation of disease cells under radiofrequency wave irradiation, with attendant advantages as set forth herein.

SUMMARY OF THE INVENTION

Radio-wave responsive particle formulations that are simultaneously useful for multiple modes of imaging and therapy are disclosed. The formulations comprise an anion-cation complex represented as D-CX, wherein C is the calcium cation, X is an anion selected from phosphate, pyrophosphate, sulphate, silicate, phosphosilicate, molybdate and carbonate. D is a dopant selected from one or more of Mo, Bi, Ba, Sr, Se, Ta, Cd, W, I, Zr, Ta, Hf, Au, Ag, Cu, Zn, Si, Fe, Mn, Al, Pt, Ce, Dy, Er, Eu, Gd, Ho, La, Lu, Nd, Pr, Pm, Sm, Sc, Tb, Tm, Yb or Y. The particles are micro- or nano-particles in the size range of 1-1000 nm. The complex is configured to generate heat under exposure to radiofrequency (RF) waves.

The particle formulation is further configured to provide simultaneous T1 and T2 contrast under magnetic resonance imaging (MRI), provide X ray absorption for CT imaging, provide near infrared (NIR) fluorescence for optical imaging, or emit radiation for nuclear imaging.

In some embodiments of the particle formulation the complex is beta-tricalcium phosphate ($Ca_3(PO_4)_2$), calcium dihydrogen phosphate ($Ca(H_2PO_4)_2$), calcium hydrogen phosphate ($CaHPO_4$), monocalcium phosphate monohydrate ($Ca(H_2PO_4).H_2O$), dicalcium phosphate dihydrate ($CaHPO_4.2H_2O$), tetracalcium phosphate ($Ca_4(PO_4)_2O$), octacalcium phosphate ($Ca_8H_2(PO_4).5H_2O$), fluorapatite ($Ca_5(PO_4)_3F$), chlorapatite ($Ca_5(PO_4)_3Cl$), or a combination thereof. In some embodiments the complex is calcium sulphate ($CaSO_4$), calcium hydrogen sulphate ($Ca(HSO_4)_2$), calcium sulphate dihydrate ($CaSO_4 \cdot 2H_2O$), calcium sulphate hemihydrate ($CaSO_4 \cdot 5H_2O$), or a combination thereof. In some embodiments the complex is calcium carbonate ($CaCO_3$), calcium bicarbonate ($Ca(HCO_3)_2$), hydrated calcium carbonate ($CaCO_3 \cdot nH_2O$, or a combination thereof. In one embodiment the complex is calcium molybdate ($CaMoO_4$). In some embodiments the complex is a calcium silicate comprising $3CaO \cdot iO_2$, $2CaO \cdot SiO_2$, $3CaO \cdot 2SiO_2$, $CaO \cdot SiO_2$, $3CaO \cdot 2SiO_2 \cdot 4H_2O$, $CaO \cdot Al_2O_3SiO_2$, $Ca_3SiO_5$, $Ca_3Si_2O_7$ or a combination thereof. In some embodiments the complex is a calcium phosphosilicate comprising 35-65 wt % $SiO_2$, 1-50 wt % $Na_2O$, 10-90 wt % $CaO$, and 1-50 wt % $P_2O_5$.

In some embodiments of the formulation, the heat generated is up to 100° C. on exposure to a radiofrequency field of frequency ranging from 1 Hz-100 GHz and power in the range 1-1000 W for a time period ranging from 0.1 seconds to 1 hour.

In various embodiments, the complex is configured to provide simultaneous T1 and T2 contrast in magnetic resonance imaging (MRI) due to doping with D at a level varying from 0.0001 to 50 atomic % of the calcium ($Ca^{2+}$). The dopant D in these embodiments comprises ions of Fe, Mn, Eu, Tb, Se, Er, Dy, Ho, Tm, Al, Mo, Ag, Au, Cu, Zn, Si, or combinations thereof.

In some aspects, the formulations are further configured to provide near-infrared fluorescence emission at the 650-1000 nm spectral region, by doping (D) with an organic molecule selected from indocyanine green or fluorescene, at levels from 0.0001 to 50 weight % of the complex.

In some aspects the formulations are further configured to provide nuclear contrast for one or more of single photon emission computed tomography, positron emission tomography (SPECT/PET) or radionuclide mediated therapy by surface labelling with a radionuclide selected from $^{153}$Sm, $^{99m}$Tc, $^{123}$I, $^{18}$F, $^{131}$I, $^{111}$In, $^{188}$Re, $^{166}$Ho, $^{90}$Y, $^{82}$Rb, $^{225}$Ac, $^{211}$At, $^{212}$Bi, $^{213}$Bi, $^{223}$Ra, $^{212}$Pb, $^{227}$Th, or $^{149}$Tb.

In other aspects, the formulations are further configured to provide CT contrast by doping with at least one impurity selected from molybdenum, bismuth, barium, strontium, tantalum, cadmium, tungsten, iodine, zirconium, tantalum, hafnium, lanthanum, gold, iron, aluminium, platinum or combinations thereof.

In various aspects, the formulation is selected from one of $(Ca,xFe,yMo)_3 (PO_4)_2$, $(Ca,xFe,yMo)_{10}(PO_4)_6(OH)_2)$, $(Ca,xFe,yMo)_2SiO_4$, or $(Ca,xFe,yMo)NaO_6PSiO_4$ where x varies from 0-50 wt %, y varies from 0-30 wt % and wherein the formulation is configured to provide T1-T2 MR contrast together with X-ray CT contrast.

In some aspects the particles have spherical or non-spherical shape with size ranging from 1 nm to 2000 nm. In some aspects the particles are further co-loaded with one or more therapeutic agents for radio-wave-triggered controlled drug release. In some embodiments the formulation is a radio-wave responsive, MR, CT, nuclear and/or NIR imageable micro-bead formulation ranging in size from 1 µm to 1 mm for vascular embolization or tissue implantation. In some embodiments the formulation is a radio-wave responsive, MR, CT, nuclear and/or NIR imageable micro-bead formulation labelled with radioisotopes for radio-embolization therapy. In some embodiments the formulation is a radio-wave responsive, MR, CT, nuclear and/or NIR imageable formulation for culturing, proliferating, differentiating, activating, or reprogramming biological cells for therapeutics.

A method of image guided radiofrequency treatment of cancer using a particle formulation in a subject with cancer is disclosed. The particles are micro- or nano-particles in the size range of 1-1000 nm. The method comprises administrating to the subject, particles comprising one of beta-tricalcium phosphate $(Ca_3(PO_4)_2)$, calcium dihydrogen phosphate $(Ca(H_2PO_4)_2)$, calcium hydrogen phosphate $(CaHPO_4)$, monocalcium phosphate monohydrate $(Ca(H_2PO_4)\cdot H_2O)$, dicalcium phosphate dihydrate $(CaHPO_4\cdot 2H_2O)$, tetracalcium phosphate $(Ca_4(PO_4)_2O)$ or octacalcium phosphate $(Ca_8H_2(PO_4)\cdot 5H_2O)$, fluorapatite $(Ca_5(PO_4)_3F)$, chlorapatite $(Ca_5(PO_4)_3Cl)$, calcium sulphate $(CaSO_4)$, calcium sulphate dihydrate $(CaSO_4\cdot 2H_2O)$ and calcium sulphate hemihydrate $(CaSO_4\cdot 5H_2O)$, calcium carbonate $(CaCO_3)$, calcium molybdate $(CaMoO_4)$, $3CaO\cdot SiO_2$, $2CaO\cdot SiO_2$, $3CaO\cdot 2SiO_2$, $CaO\cdot SiO_2$, $3CaO\cdot 2SiO_2\cdot 4H_2O$, $CaO\cdot Al_2O_3\cdot 2SiO_2$, $Ca_3SiO_5$, $Ca_3Si_2O_7$, a calcium phosphosilicate with compositions ranging from 35-65 wt % $SiO_2$, 1-50 wt % $Na_2O$, 10-90 wt % $CaO$, 1-50 wt % $P_2O_5$, $Ca,xFe,yMo)_3 (PO_4)_2$, $(Ca,xFe,yMo)_{10}(PO_4)_6 (OH)_2)$, $(Ca, xFe,yMo)_2SiO_4$, $(Ca,xFe,yMo)NaO_6PSiO_4$ or combinations thereof. The nanoparticles may be doped with a dopant selected from a chloride, bromide, iodide, fluoride, nitrate, sulphate, carbonate or oxide salt of a metal selected from one or more of Mo, Bi, Ba, Sr, Ta, Se, Cd, W, I, Zr, Ta, Hf, La, Au, Fe, Al, Pt, Ce, Dy, Er, Eu, Gd, Ho, La, Lu, Nd, Pr, Pm, Sm, Sc, Tb, Tm, Yb, or Y, or a dye comprising indocyanine green or fluorescene, and conjugated with an agent comprising one or more of a radiolabel, a bisphosphonate drug, a capping agent or a targeting ligand. The method then involves contacting the particles with the cancer cells and then imaging the particles-containing cancer cells by one or more of magnetic resonance, nuclear, near infrared, or computed tomography to detect the location of the cancer cells. A therapeutic dose of radiofrequency waves is then applied to the cancer cells to ablate the cells and RF-induced delivery of the conjugated agent from the particles to the cancer cells may additionally be effected.

The method of treatment in some aspects may further comprise simultaneous or separate dual mode (T1-T2) MR, nuclear imaging-guided cell culture and tissue regeneration. In some aspects the method may further comprise nuclear imaging-guided radio-chemoembolization and radiation therapy. In further aspects the method may comprise image guided modulation, activation, suppression, re-programming, editing of cells and immunotherapy for treating a disease condition. In some aspects the method may comprise cancer detection and therapy. In some aspects the method may comprise stimulating, treating, carrying and delivering, one or more of stem cells, induced pluripotent stem cells, differentiated cells, immune cells, bacteria, or viruses.

The method of treatment in some embodiments may further comprise image guided delivery of a therapeutic agent comprising a chemodrug, siRNA, DNA, RNA, a peptide, a protein, or a gene. In various embodiments the treatment may comprise administrating the particles subcutaneously, orally, intravenously or intraperitoneally, or implanting as gels, beads or scaffolds. In various embodiments the particles activate immune response against the cancer cells in the subject.

This and further aspects are set forth herein.

BRIEF DESCRIPTION OF THE DRAWINGS

The invention has other advantages and features which will be more readily apparent from the following detailed description of the invention and the appended claims, when taken in conjunction with the accompanying drawings, in which:

FIG. 4A schematic of Fe-nCX (X=phosphate) where a few $Ca^{2+}$ atoms are replaced by doped $Fe^{3+}$.

FIG. 4B TEM image showing particles of size ~10 nm.

FIG. 5 shows Zeta potential data peaked at ~15 mV for $Fe^{3+}$ doped calcium phosphate nanoparticles.

FIG. 8A and FIG. 8B show in vivo (FIG. 8A) T1 weighted and (FIG. 8B) T2 weighted MRI of Wistar rat before and after Fe-nCX (X=phosphate) injection.

FIG. 8C and FIG. 8D show enhancement of both T1 and T2 contrast after sample injection (FIG. 8C) axial liver section before sample injection, and (FIG. 8D) axial liver section 30 minutes after sample injection. FIG. 8E shows T2 mapping data averaging 3 ROI selected in the axial sections before and 1 hr after injection FIG. 9A T2 weighted MRI of wistar rat over a period of 96 hours after intravenous injection of Fe-nCX (X=phosphate)

FIG. 10A shows T2 weighted MR image (coronal section) of subcutaneous tumour before sample injection, while

FIG. 17A shows proliferation assay of rat mesenchymal stem cells treated with Fe-nCX (X=phosphate), FIG. 17B illustrates rMSC treated with 100 μg/mL of Fe-nCX for 6 hours, FIG. 17C shows MRI of cell pellet of unlabelled rMSC and Fe-nCX labelled rMSC, FIG. 17D illustrates MRI of rat brain injected with unlabelled cells and FIG. 17E is MRI of rat brain injected with labelled cells, with injected regions marked.

FIG. 20A and FIG. 20B are SEM images of nanoparticle uptake by macrophages, representing immune cells.

FIG. 20C shows FACS analysis of cytokine induction of macrophage after PBS treatment and FIG. 20D is FACS analysis showing increased cytokine induction by nanoparticle treated macrophages.

DETAILED DESCRIPTION OF THE EMBODIMENTS

Figure 1:
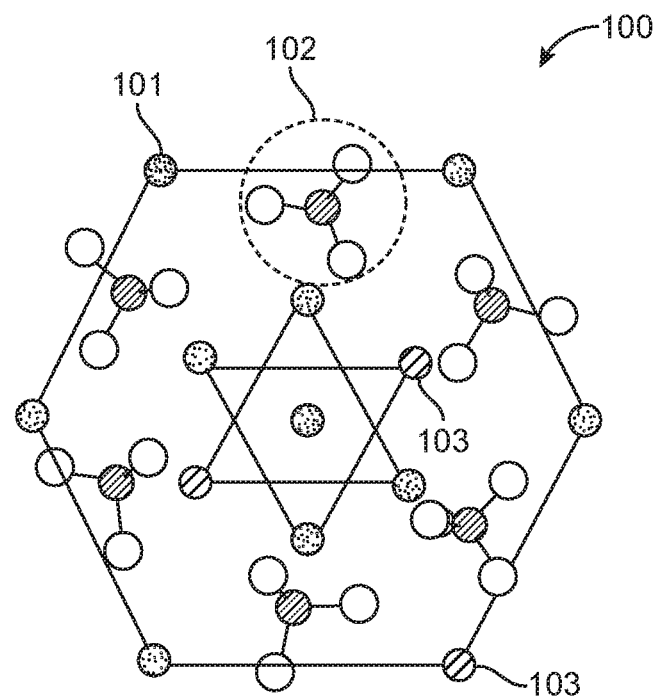
FIG. 1 illustrates in one embodiment a system of radio-wave responsive particles for tumour ablation.

While the invention has been disclosed with reference to certain embodiments, it will be understood by those skilled in the art that various changes may be made and equivalents may be substituted without departing from the scope of the invention. In addition, many modifications may be made to adapt to a particular situation or material to the teachings of the invention without departing from its scope.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

The invention in its various embodiments discloses nanoparticles comprising doped phosphate, sulphate, phosphosilicate, or bioactive glass compounds of calcium, termed as 'D-nCX', where D represents dopant ions, n indicates nanometer size, C is calcium, X is anions such as phosphate, pyrophosphates, sulphate, silicate, carbonate, molybdate, or phosphosilicate. The nanoparticles produce heat (hyperthermia) under radio-wave (1 KHz-1000 GHz) exposure together with providing magnetism suitable for contrast imaging in MRI, X-ray absorption for computed tomography, near-infrared optical fluorescence for optical imaging, and/or radio-isotope emission for nuclear imaging or therapy. The nanoparticles can also be incorporated into micro-beads or other 3 dimensional scaffolds for image guided (MRI, CT, NIR, nuclear) tissue regeneration, vascular or tumor embolization, and/or chemo/radio-embolization. The nanoparticles or associated systems can also be used for image guided drug delivery, gene delivery, siRNA delivery, stem cell labeling, activation, suppression or re-programming of immune cells.

The invention in one embodiment proposes a system 100 of calcium-based compounds D-CX that can be formed into nanoparticle formulations as disclosed in FIG. 1. System 100 comprises the complex D-CX calcium (also denoted as C) as the cation 101 reacted with an anionic group 102, denoted as X in the description. The system comprises dopant 103, intended to provide various types of functionality to the formulations (also denoted as D). In various embodiments, the anionic group 102 is selected from phosphate, pyrophosphate, sulphate, silicate, phosphosilicate, molybdate and carbonate. Dopant 103 is a metal selected from one or more of Mo, Bi, Ba, Sr, Ta, Cd, W, I, Zr, Ta, Hf, La, Au, Fe, Al, Pt, Ce, Dy, Er, Eu, Gd, Ho, La, Lu, Nd, Pr, Pm, Sm, Sc, Tb, Tm, Yb or Y. The particulate system 100 is configured to generate heat under radiofrequency wave exposure.

In various embodiments the system 100 is also configured to provide other functionalities for imaging such as simultaneous T1 and T2 contrast under magnetic resonance imaging (MRI), X ray absorption for CT imaging, near infrared (NIR) fluorescence for optical imaging or emit radiation for nuclear imaging. The functionalities are provided by incorporating a suitable combination of dopants 103 in the formulation.

In various embodiments the complex of system 100 is a phosphate of calcium such as beta-tricalcium phosphate ($Ca_3(PO_4)_2$), calcium dihydrogen phosphate ($Ca(H_2PO_4)_2$), calcium hydrogen phosphate ($CaHPO_4$), monocalcium phosphate monohydrate ($Ca(H_2PO_4)_2 \cdot H_2O$), dicalcium phosphate dihydrate ($CaHPO_4 \cdot 2H_2O$), tetracalciumphosphate ($Ca_4(PO_4)_2O$), octacalciumphosphate ($Ca_8H_2(PO_4)_6 \cdot 5H_2O$), fluorapatite ($Ca_5(PO_4)_3F$), chlorapatite ($Ca_5(PO_4)_3Cl$), or combinations thereof. In some embodiments the complex 100 is a sulphate of calcium such as calcium sulphate (CaSO$_4$), calcium hydrogen sulphate (Ca(HSO$_4$)$_2$), calcium sulphate dihydrate (CaSO$_4$·2H$_2$O), calcium sulphate hemihydrate (CaSO$_4$·5H$_2$O), or combinations thereof. In various embodiments the complex 100 is a carbonate of calcium such as calcium carbonate (CaCO$_3$), calcium bicarbonate (Ca(HCO$_3$)$_2$), hydrated calcium carbonate (CaCO$_3$·nH$_2$O, or a combination thereof. In one embodiment the complex 100 is calcium molybdate (CaMoO$_4$). In some embodiments the complex 100 is a calcium silicate such as 3CaO·SiO$_2$, 2CaO·SiO$_2$, 3CaO·2SiO$_2$, CaO·SiO$_2$, 3CaO·2SiO$_2$·4H$_2$O, CaO·Al$_2$O$_3$·2SiO$_2$, Ca$_3$SiO$_5$, Ca$_3$Si$_2$O$_7$, or a combination thereof. In some embodiments the complex 100 is a calcium phosphosilicate or bioglass comprising 35-65 wt % SiO$_2$, 1-50 wt % Na$_2$O, 10-90 wt % CaO, and 1-50 wt %/P$_2$O$_5$.

In various embodiments the complex 100 is configured to respond to RF wave exposure by heating. In some embodiments the heat generated is up to 100° C. on exposure to a radiofrequency field of frequency ranging from 1 Hz-100 GHz. The power applied may be in the range 1-1000 W for a time period ranging from 0.1 seconds to 1 hour.

In various embodiments where the particles are intended for ablating cancer tissue, the particles incorporating the complex 100 are configured to be nanoparticles having spherical or non-spherical shape with size ranging from 1 nm to 2000 nm. In some embodiments where the particles are intended to be implanted into a human or animal body for tissue regeneration, the particles could be microparticles with size ranging from a few microns to a few mm.

In some embodiments the complex 100 is configured to provide simultaneous T1 and T2 contrast in magnetic resonance imaging (MRI). In embodiments in which simultaneous T1 and T2 contrast is provided, the particles carry dopant D at a level varying from 0.0001 to 50 atomic % of the calcium (Ca$^{2+}$) ion content. Dopant D comprises ions of Fe, Mn, Eu, Tb, Er, Dy, Ho, Tm, Al, Mo, Ag, Au, Cu, Zn, Si, or combinations thereof.

In some embodiments the complex 100 is configured to provide near-infrared (NIR) fluorescence emission in the 650-1000 nm spectral region. The NIR emission is provided by doping (D) with an organic dye molecule. The organic dye could be any dye that provides fluorescence in the relevant spectral range. The dopant could be selected from indocyanine green or fluorescene at levels from 0.0001 to 50 weight % of the complex.

In some embodiments the complex 100 is further configured to provide CT contrast by doping with suitable species. The CT contrast is provided by doping with an impurity ion such as molybdenum, bismuth, barium, strontium, tantalum, cadmium, tungsten, iodine, zirconium, tantalum, hafnium, lanthanum, gold, iron, aluminium, platinum or combinations thereof.

In various embodiments the complex 100 is further configured to provide nuclear contrast by emission of radiation. The emission is provided to enable detection of the complex 100 using techniques such as single photon emission computed tomography or SPECT, positron emission tomography or PET, or radionuclide mediated therapy. In various embodiments the nanoparticles or microparticles of the invention are tagged for nuclear contrast by surface labelling with a radionuclide selected from $^{153}$Sm, $^{99m}$Tc, $^{123}$I, $^{18}$F, $^{131}$I, $^{111}$In, $^{188}$Re, $^{166}$Ho, $^{90}$Y, $^{82}$Rb, $^{225}$Ac, $^{211}$At, $^{212}$Bi, $^{213}$Bi, $^{223}$Ra, $^{212}$Pb, $^{227}$Th, or $^{149}$Tb.

In some embodiments, the complex 100 is a radio-wave responsive, MR, CT, nuclear and/or NIR imageable microbead formulation ranging in size from 1 μm to 1 mm for vascular embolization or tissue implantation. In alternate embodiments the complex 100 may be further functionalized for radio-embolization therapy. In some embodiments the complex 100 may be surface-conjugated with a chemodrug, siRNA, DNA, RNA, a peptide, a protein, a gene or a gene fragment.

Figure 2:
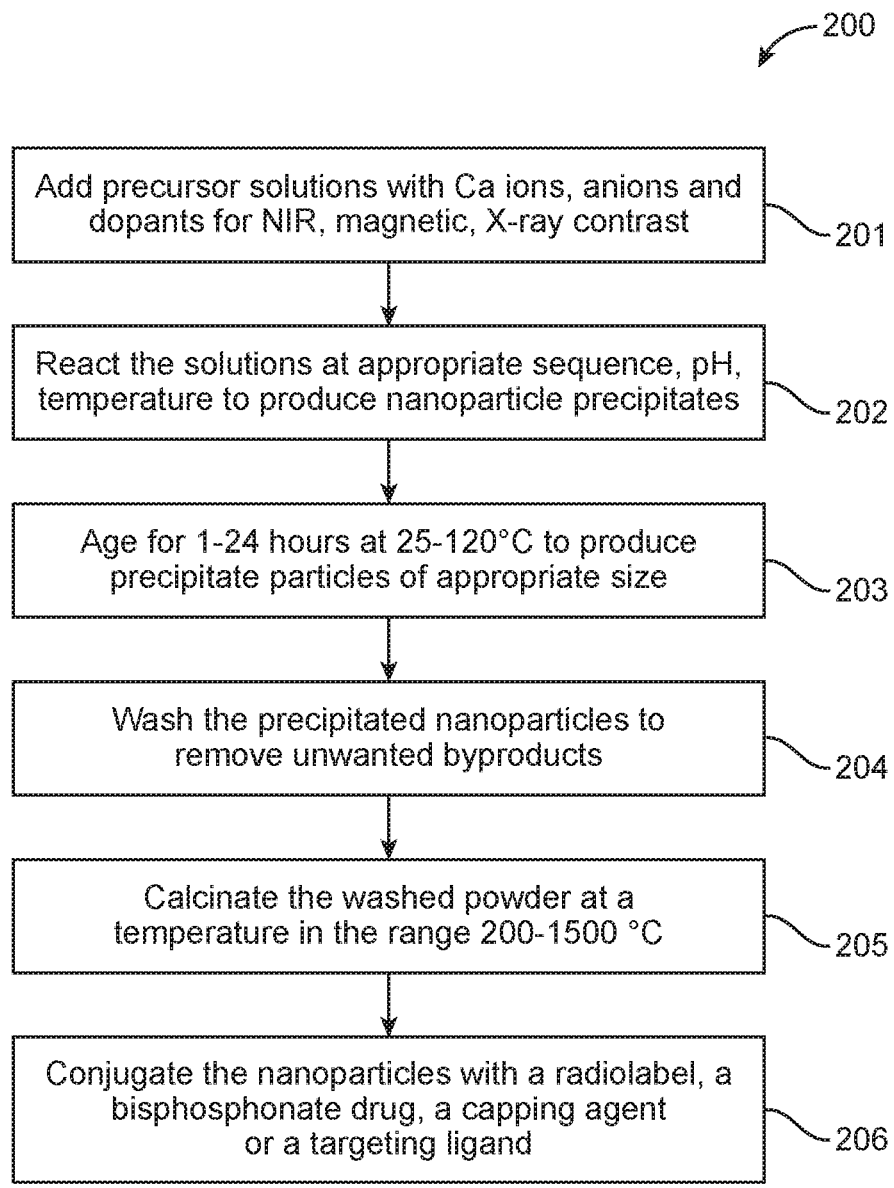
FIG. 2 is a schematic of a method of preparing radio-wave responsive particles for tumour ablation.

In various embodiments, the invention discloses in FIG. 2 methods 200 for preparing the nanoparticle formulations 100 disclosed in FIG. 1. The method 200 involves in step 201, adding and mixing precursor solutions Part A containing Ca ions, Part B containing anion species, Part C containing hydroxyl ions (OH$^-$, a surfactant solution in Part D and an aqueous solution containing a dopant and additionally a dye in Part E to a container and reacting them (step 202) to form the precipitate particles. Further, in step 203, the precipitate particles are allowed to grow by aging. The reacting step 202 and the aging step 203 may be carried out for 1-24 hours at a temperature in the range 25-120° C. The next step 204 involves washing the precipitate particles with de-mineralized water to remove solutes and reaction products. The particles are thereafter calcined (step 205) at a temperature in the range 200-1500° C. to obtain dry powder. In a further step 206, the dry powder particles are reconstituted using water or phosphate buffer saline and surface-conjugated with radiolabels, bisphosphonate drugs, capping agents or targeting ligands to provide additional functionalities depending on the application, to obtain the particle formulation.

In various embodiments the solution containing calcium ions in Part A is prepared from water soluble, miscible or dispersible salts of calcium hydroxide, chloride, bromide, iodide, fluoride, nitrate, sulphate, carbonate or oxide.

In various embodiments, the precursor compound in Part B containing an anion, is formed from a species selected from phosphate, pyrophosphate, sulphate, carbonate, molybdate, silicate, and phosphosilicate.

For forming calcium phosphate nanoparticles, the precursor solution for phosphate anions in Part B in various embodiments is formed from a water soluble or miscible salt of a phosphate. The phosphate ion source could be a phosphate of sodium—Na$_3$PO$_4$, Na$_2$HPO$_4$, NaH$_2$PO$_4$, potassium—K$_3$PO$_4$, K$_2$HPO$_4$, KH$_2$PO$_4$, lithium—Li$_3$PO$_4$, Li$_2$HPO$_4$, LiH$_2$PO$_4$, ammonium—(NH$_4$)$_3$PO$_4$, (NH$_4$)$_2$HPO$_4$, NH$_4$H$_2$PO$_4$ or alternatively, phosphoric acid, or a combination thereof.

For forming calcium sulphate nanoparticles, the precursor solution for sulphate anions in Part B in various embodiments is prepared using sulphuric acid or sodium sulphate salt or a combination thereof.

To prepare calcium carbonate nanoparticles, the precursor solution containing carbonate ions in Part-B in various embodiments is constituted of a soluble carbonate salt or carbonic acid. The carbonate salt could be sodium carbonate, potassium carbonate or ammonium carbonate, or combinations thereof.

To prepare calcium molybdate nanoparticles, the precursor solution containing molybdate ions in Part B in various embodiments could be constituted from a soluble salt of molybdenum. The salt could be sodium molybdate, potassium molybdate, ammonium molybdate, or combinations thereof.

To prepare calcium silicate particles, the anion source of Part B in various embodiments could be either silica or a soluble silicate salt. The soluble silicate salt could be sodium silicate, potassium silicate, calcium silicate, or combinations thereof.

In various embodiments, the precursor compound containing hydroxyl anions in Part C is formed by a hydroxide salt of either sodium, potassium, lithium, ammonium or calcium.

To prepare calcium phosphosilicate or bioglass particles, Part-B in various embodiments includes silica, tetraethyl orthosilicate (TEOS) or a soluble silicate salt, while the solution in Part C includes a phosphate source. The soluble silicate salt could be sodium silicate, potassium silicate, or combinations thereof. The phosphate source in Part-C could be triethyl phosphate, diammonium hydrogen phosphate, sodium monophosphate, sodium diphosphate, sodium polyphosphate, phosphorus pentoxide, or combinations thereof.

In some embodiments the surfactant solution in Part D, is formed by an aqueous solution of monosodium, disodium or trisodium citrate or citric acid. In some embodiments the solution may additionally include a polymer such as polyethylene glycol, poly-L lactic acid, polyethylene imine, or poly(lactic-co-glycolic acid).

In various embodiments, the dopant ions in Part E are configured to provide various functionalities such as T1 and T2 magnetic contrast, X-ray absorption for CT imaging, or near-infrared fluorescence for optical imaging, at a level varying from 0.0001 to 50 atomic % of the calcium ($Ca^2$).

In some embodiments the T1 and T2 magnetic contrast is provided by including in Part E a solution containing ions such as manganese (II), iron(II), iron (III), gadolinium (III) or other lanthanides such as Dy, Er, Eu, Ho, La, Lu, Nd, Pr, Pm, Sm, Sc, Tb, Tm, Yb or Y, or Al, Mo, Ag, Au, Cu, Zn, or Si, or combinations thereof. In further embodiments, the CT contrast is provided by adding in Part E a solution containing ions of molybdenum, bismuth, barium, strontium, tantalum, cadmium, tungsten, iodine, zirconium, tantalum, hafnium, lanthanum, gold, iron, aluminium, or platinum or combinations thereof. In another embodiment, Part E could further comprise a solution containing dye molecules that gives near-infrared fluorescence to the nanoparticle. The dye molecules could be NIR emitting dyes such as indocyanine green (ICG) or fluorescene.

In some embodiments the doped nanoparticle is surface conjugated during the reconstitution step 206 of the method to provide therapeutic effects or radiolabelling or other therapeutic property. In some embodiments surface labelling with a radionuclide selected from $^{153}$Sm, $^{99m}$Tc, $^{123}$I, $^{18}$F, $^{131}$I, $^{111}$In, $^{188}$Re, $^{166}$Ho, $^{90}$Y, $^{82}$Rb, $^{225}$Ac, $^{211}$At, $^{212}$Bi, $^{213}$Bi, $^{223}$Ra, $^{212}$Pb, $^{227}$Th, or $^{149}$Tb is done through ligands such as bisphosphonates. The radionuclide labelling is intended to provide nuclear contrast for a technique such as single photon emission computed tomography or SPECT, positron emission tomography (PET) or radionuclide mediated therapy. In some embodiments the nanoparticles may be co-loaded with therapeutic agents for radio-wave-triggered controlled drug release.

Figure 3:
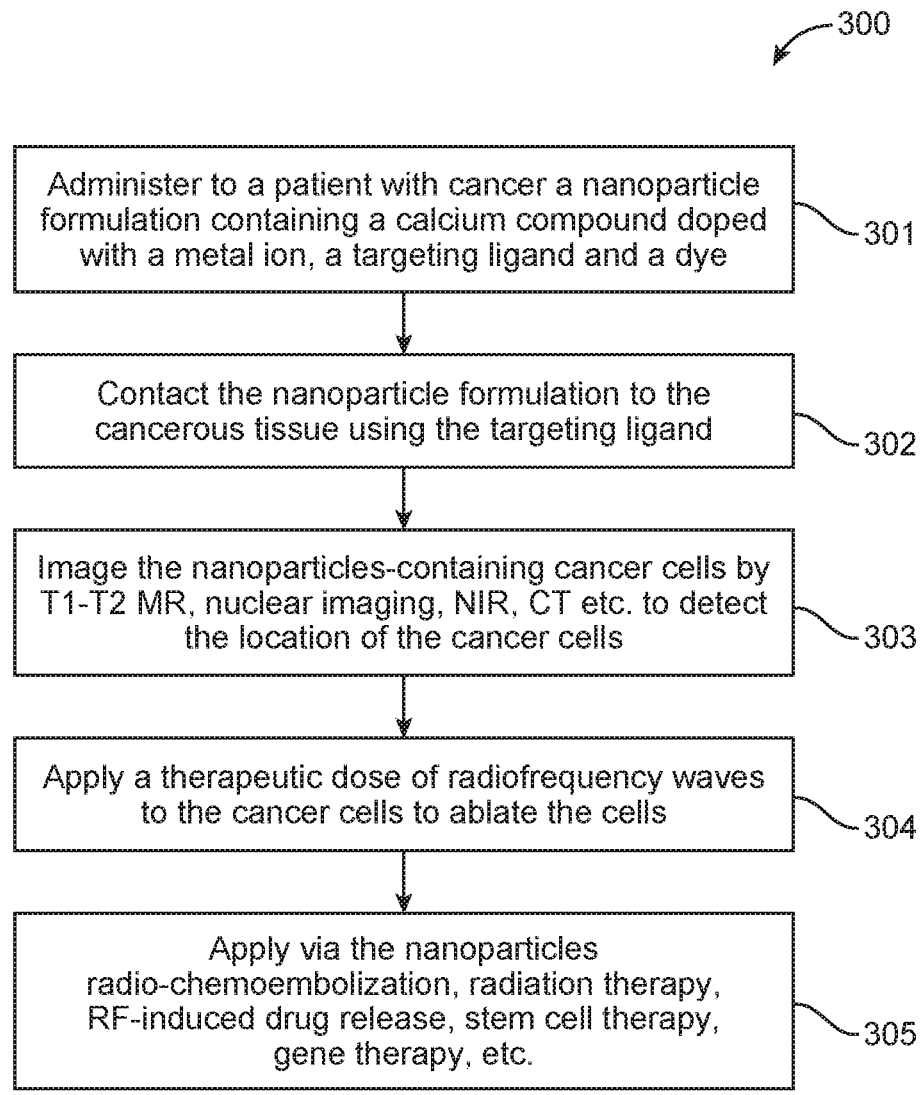
FIG. 3 illustrates exemplary methods of treatment using RF-responsive particles for tumour ablation.

The invention further comprises methods of treatment using the system 100 disclosed with reference to FIG. 1 and method of preparation with reference to FIG. 2. In some embodiments, methods of treatment 300 as disclosed in FIG. 3 comprise the step 301 of administering to a patient with cancer a particle formulation 100 containing a calcium compound doped with a metal ion, a targeting ligand and a dye, functionalized as illustrated in previous embodiments. In various embodiments the step 301 may comprise administrating the particles subcutaneously, orally, intravenously or intraperitoneally. In some embodiments in step 301 they may also be implanted as gels, beads or scaffolds. In the next step 302, the particles are contacted with the cancer cells. The target area is then visualized (step 303) by imaging the particles-containing cancer cells by a method such as magnetic resonance, nuclear, near infrared, or computed tomography to detect the location of the cancer cells. The visualization in step 303 may be simultaneous or separate dual mode (T1-T2) MR, nuclear imaging or optical imaging using the functionality provided by system 100. In the next step 304, RF ablation is provided in a therapeutic dose to effect ablation to the contacted cancer cells. Concurrently or subsequently, in step 305, the RF wave exposure may also trigger release of one or more conjugated agents, markers or other species to the cancer cells.

Currently, in clinics, separate contrast agents are being used for T1 and T2 weighted imaging. Gadolinium complexes are the most widely used T1 contrast agents whereas super-paramagnetic iron oxide nanoparticles (SPIONS) are used as T2 contrast agents. Usually T1 weighted imaging is carried out for anatomical imaging purposes whereas T2 weighted imaging is carried out for obtaining pathological or functional details. The treatment modalities provided by the system 100 according to embodiments of the method of treatment 300 are further illustrated. In one embodiment of the method 300, the unique advantage of the inventive particles of system 100 is that using this single system therapists can image a diseased condition utilizing both T1 and T2 (bright and dark) MR contrast and also enhance the RF response of the diseased tissue. In an alternate embodiment of the method 300, the therapists can also switch over to X ray contrast using the same system because the same nanoparticles can give both contrast simultaneously or separately with MRI, as the particles 100 may be co-doped with X ray absorbing ions. In effect, embodiments of the method 300 disclosed herein provide for multi-modal image guided RF hyperthermia therapy.

In some embodiments of the method 300, in addition to MRI or CT contrast, the particles can also be used to provide near-infrared contrast for optical imaging. Near infrared contrast is achieved by co-doping organic dyes such as indocyanine within the particles 100 together with magnetic or CT contrast dopants to provide additional property of near-infrared fluorescence emission.

In other aspects of the method 300, bisphosphonate conjugated nuclear labels, as illustrated in earlier embodiments, for example 99Technitium-MDP, are efficiently tagged on the calcium atoms of D-nCX nanoparticles through calcium-phosphonate linkage, to provide nuclear contrast. Combinatorial imaging using MRI-CT together with nuclear methods like SPECT-PET is then done to provide simultaneous high definition anatomical, physiological and functional information about the diseases like cancer and image guided application of multiple radio-wave mediated processes. The radio-wave mediated processes could be one or more of hyperthermia, drug-delivery, gene delivery, or other therapeutics. The system 100 and the method 300 in the various embodiments not only provide contrast imaging but also provide radio-wave responsiveness that is useful for multitude of applications such as hyperthermia, RF triggered therapeutic release, cell activation, tissue regeneration etc.

In further aspects of the method 300, the nanoparticles are used to form micro-beads of size varying from 1-1000 microns for image guided (dual mode MRI, CT, NIR and/or nuclear) embolization, chemo-embolization or radio-embolization of tumor or vasculature. For example, the method 300 may comprise embolization of the feeding artery to a tumor. The procedure of embolization is done by injecting micro-beads through a trans-arterial catheterization under the guidance of X-ray CT or MRI. The excellent X-ray and MR contrast of the disclosed system 100 provide unique advantages over existing agents and can be loaded within polymeric micro-beads for use in embolization therapy. The same microbeads can also be surface conjugated or labeled with therapeutic radio-nucleotides for image guided nuclear medicine or embolization.

In yet other aspects of the method 300, the micro-beads formed from D-CX nanoparticles are co-loaded with chemodrugs, siRNA, therapeutic peptides, proteins, small molecules, genes, etc. to conduct RF-triggered drug release. Due to the radio-wave hyperthermia response of the embedded nanoparticles, the microbeads or scaffolds are configured to expand and contract with respect to the application of RF wave and thermal-energy leading to the triggered drug release. In alternative embodiments, these nanoparticles can be co-loaded into drug loaded thermo-responsive polymeric nanoparticles such that with exposure to RF wave, the increase in temperature triggers the drug release.

In various embodiments of the method 300, these nanoparticles of the system 100, owing to their MR, X-ray, NIR contrast, are used for image guided tissue regeneration. In some embodiments, these nanoparticles are loaded into porous micro-beads or 3D polymeric scaffolds where stem cells, or differentiated organ cells or tissues are regenerated and the same are monitored in vivo using different imaging modalities such as MRI or CT. The RF responsivity of nanoparticles can be used to stimulate the cells for better proliferation and differentiation into various tissues and phenotypes.

In various aspects of the method 300, the RF responsive nanoparticles of system 100 are conjugated with immunotherapeutic molecules such as cancer antigens, peptides or small molecules and used as image guided immunotherapeutic adjuvant or immune cell stimulating/suppressing agents. Under RF exposure, these nanoparticles may stimulate the controlled or triggered delivery of immunologic agents together with producing heat energy at local tissue regions that may attract immune cells to the site of heating and hence externally controllable immune response may be obtained for various therapeutic scenarios such as cancer or autoimmune disease.

In other embodiments of method 300, the system 100 is labelled with stem cells or other types of cells for their image guided delivery and activation in vivo. For example, human mesenchymal stem cells can be labelled with MR-CT imageable D-CX nanoparticles and injected into the disease site or intravenously such that the kinetics of the cells can be mapped using MRI or CT. Additionally, owing to the RF response, the injected cells can be activated using external RF trigger. For example, an antigen or peptide released from the radio-responsive NPs under RF exposure may trigger immune cell activation of differentiation of stem cells.

While the invention has been disclosed with reference to certain embodiments, it will be understood by those skilled in the art that various changes may be made and equivalents may be substituted without departing from the scope of the invention. In addition, many modifications may be made to adapt to a particular situation or material the teachings of the invention without departing from its scope as further explained in the following examples, which however, are not to be construed to limit the scope of the invention as delineated by the claims

EXAMPLES

Figure 6A:
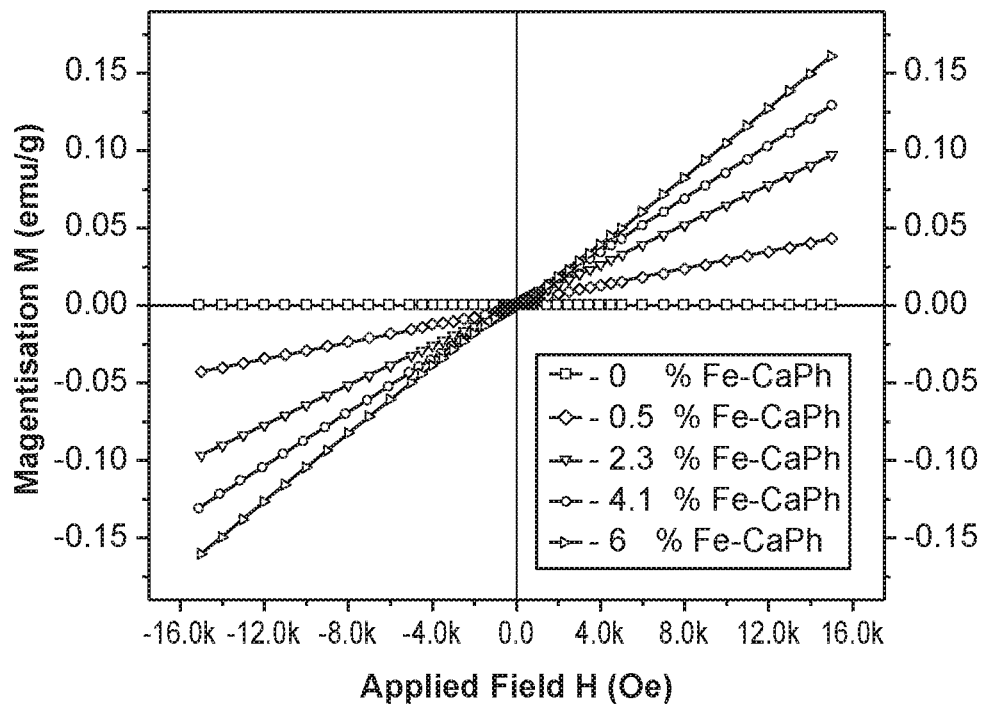
FIG. 6A shows VSM data and FIG. 6B shows magnetic susceptibility data of different batches of Fe-nCX (X=phosphate) doped with varying concentration of $Fe^{3+}$.
Figure 6B:
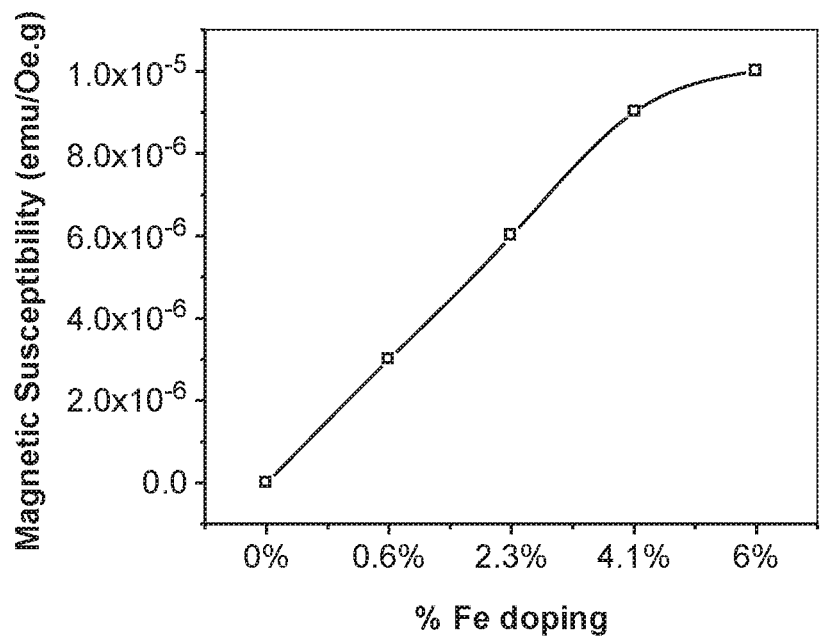

Example—1 Preparation of Iron Doped Calcium Phosphate Nanoparticles (nCP: Fe) for Dual T1-T2 Magnetic Contrast Guided Radiofrequency Ablation of Tumor—Synthesis and Characterization 20 mL of 0.5 M calcium chloride ($CaCl_2$, Sigma, USA) was mixed with 20 mL of 0.2 M trisodium citrate ($Na_3C_6H_5O_7$, Fisher Scientific, India) and 0.1 M $FeCl_3$ (Sigma, USA). Volume of 0.1 M $FeCl_3$ added was varied as per the required percentage of doping. 5 mL of 0.3 M diammonium hydrogen phosphate ($(NH_4)_2HPO_4$, S.D Fine Chemicals, India) mixed with 0.2 mL of 3 N ammonium hydroxide ($NH_4OH$, Fisher Scientific, India) was added drop wise to the above mixture of $CaCl_2$, $Na_3C_6H_5O_7$ and $FeCl_3$ under constant stirring to obtain Fe doped calcium phosphate nanoparticles, Fe-nCX (X=phosphate). The precipitate was washed 4 times in hot distilled water by centrifugation at 8500 rpm for 15 minutes and redispersed in PBS. FIG. 4A shows the schematic of Fe-nCX, wherein $Fe^{3+}$ replaces $Ca^{2+}$ in the calcium phosphate crystal lattice. Successful doping of $Fe^{3+}$ within nCP is clearly indicated by the yellow color of Fe-nCX solution. TEM shows uniform size distribution of ~10 nm (FIG. 4B). The efficiency of $Fe^{3+}$ doping, estimated by ICP analysis, showed that on an average ~40% of the added ions were doped within nCP (FIG. 5A). In order to investigate if doped $Fe^{3+}$ was leaching out of Fe-nCX, the final supernatant obtained after fourth wash was analyzed. $Fe^{3+}$ level in supernatant was below the level of detection by ICP that indicated $Fe^{3+}$ is efficiently doped within nCP matrix. The zeta potential of Fe-nCX was estimated to be −15 mV (FIG. 5B) which is attributed to presence of citrate ions on the surface of Fe-nCX. Magnetic property of Fe-nCX analyzed by VSM, showed linear increase in magnetization with external field indicating paramagnetic behavior (FIG. 6A) compared to diamagnetic property of undoped nCP. The paramagnetic nature of Fe-nCX is conferred by $Fe^{3+}$ due to the presence of a lone unpaired electron in its 3d orbital. As expected, increase in $Fe^{3+}$ doping concentration from 0.5 to 6 wt % resulted in enhancement of the paramagnetic behavior (FIG. 6A) and magnetic susceptibility (FIG. 6B).

Figure 7A:
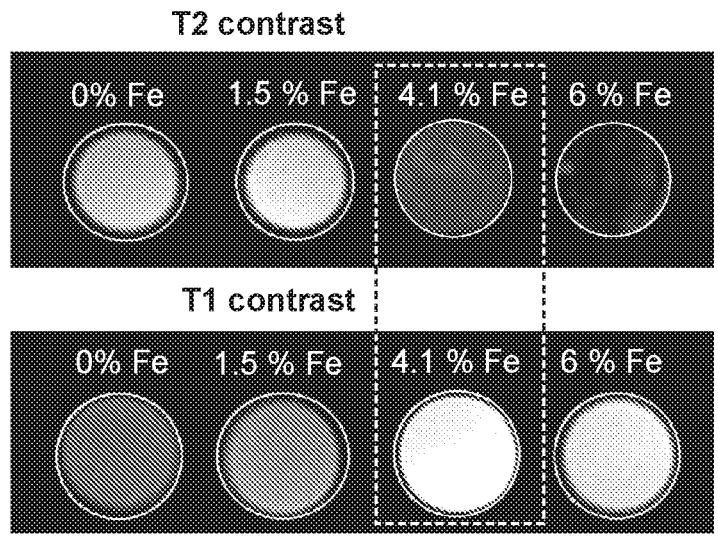
FIG. 7A shows T2 and T1 weighted MR contrast of 1.25 mg/mL of Fe-nCX (X=phosphate) doped with varying concentration of $Fe^{3+}$, dispersed in agar phantom.
Figure 7B:
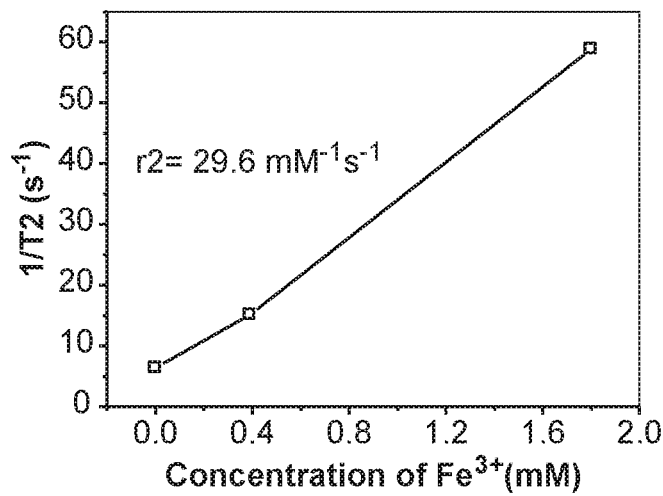
FIG. 7B and FIG. 7C show r2 and (FIG. 7C) r1 relaxivity plot of 4.1 at % $Fe^{3+}$ doped Fe-nCX respectively.
Figure 7C:
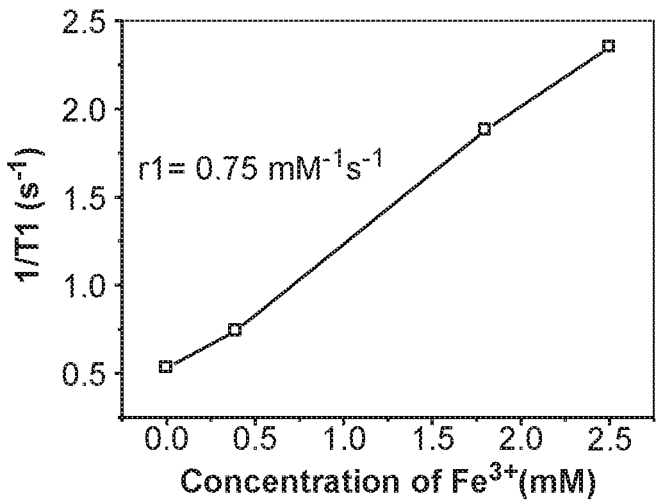

Increase in $Fe^{3+}$ dopant concentration from 1.5 to 6 wt % resulted in enhancement of T2 contrast intensity (FIG. 7A) whereas T1 contrast increased up to a concentration of 4.1 wt % after which it reduced. Thus we identified that at an optimum doping concentration of 4.1 wt %, Fe-nCX provided an efficient dual mode T1/T2 contrast in MRI. 4.1 wt % Fe doped nCP will be hereafter mentioned as Fe-nCX. Mapping studies were carried out to estimate the T1 and T2 relaxivity values. FIG. 7B, 7C show variation in T2 and T1 relaxation time with increase in nanoparticle concentration of Fe-nCX. T1 relaxivity value (r1) of Fe-nCX was estimated as 0.75 $mM^{-1}s^{-1}$ and T2 relaxivity value (r2) as 29.6 $mM^{-1}s^{-1}$. Although the obtained r1 and r2 values are lower than that of clinically available contrast agents (r1 value Gd-DOTA33 at 7 T is 2.8 $mM^{-1}s^{-1}$, r2 value of FeO at 1.5 T is 213 $mM^{-1}s^{-1}$), considering the intratumoral injection of Fe-nCX, the obtained contrast will be sufficient for clinical applications.

Figure 9A:
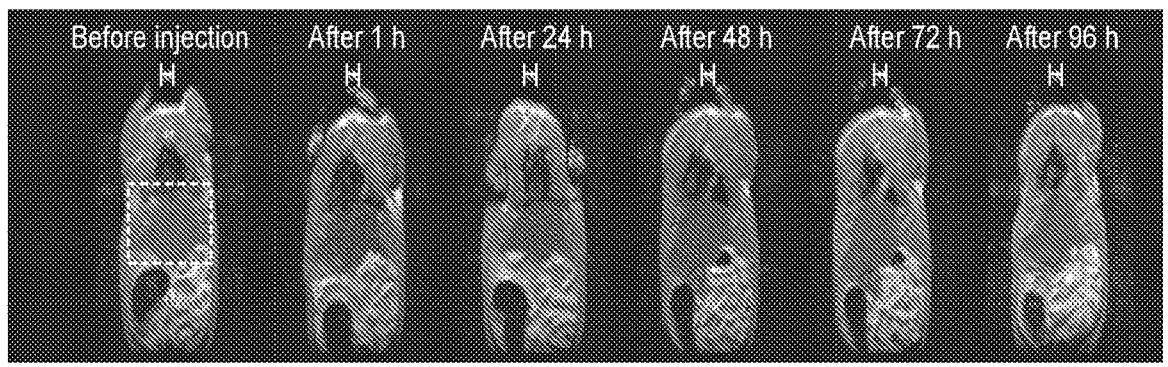
FIG. 9B shows corresponding axial liver sections over a period of 96 hrs.
FIG. 9C illustrates variation in T2 time of liver over a period of 96 hours after Fe-nCX injection and FIG. 9D shows Fe content in different organs estimated by ICP analysis.
Figure 9B:
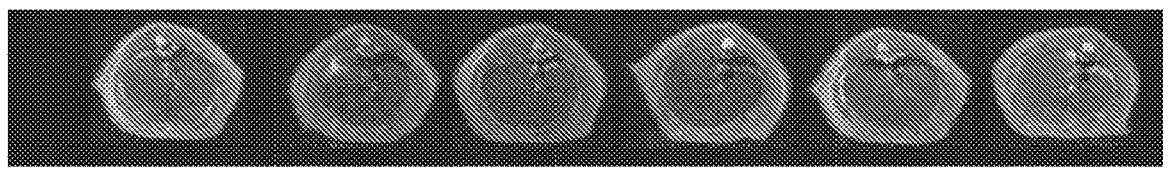
Figure 9C:
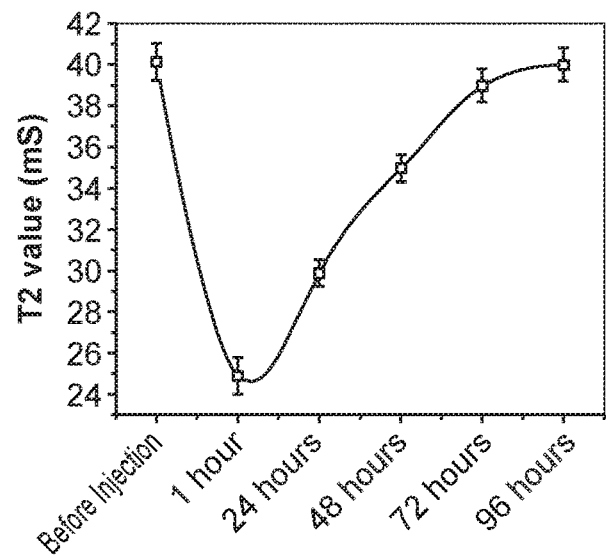
Figure 9D:
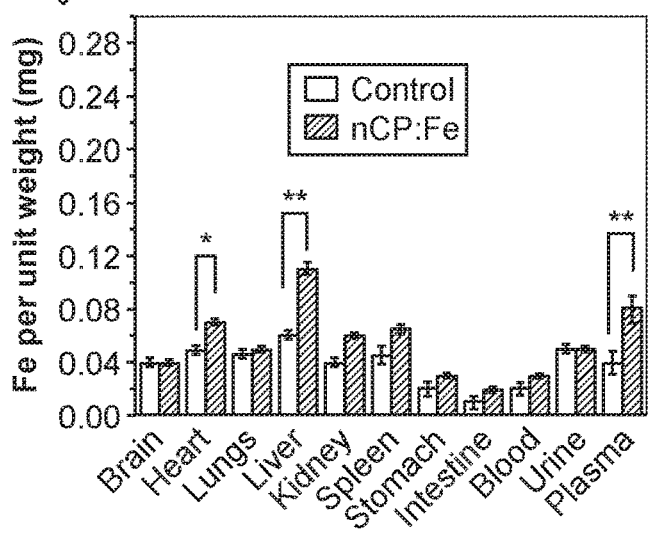

Preparation of Chitin Nanogels (CN):

Chitin solution was prepared by adding chitin to saturated $CaCl_2$ solution in methanol and dissolving by vigorous stirring using overhead stirrer for nearly 48 h at room temperature. 0.05% chitin solution was prepared by using this method and they were further used for the preparing nCN by employing controlled regeneration chemistry and wet milling methods. The preparation and characterization of this control nCN were done using usual methods Example 2—Demonstration of In Vivo Dual Mode T1 and T2 Contrast 1 hour after Fe-nCX(X=phosphate) injection, an enhancement of both T1 and T2 contrast was observed especially in the liver and heart region (shown in white dotted box: FIG. 8A, 8B). Axial T2 weighted images of liver sections before (FIG. 8C) and after (FIG. 8D) Fe-nCX injection clearly showed enhancement in T2 contrast intensity after sample injection that was also reflected in T2 mapping data (FIG. 8E) obtained from selected ROI (white circles in FIG. 8B, 8C). Reduction in T2 contrast in liver was associated with reduction of T2 relaxation time from 40 ms to 25 ms. To evaluate the biodistribution of Fe-nCX, MRI of sample injected animal was carried out over a period of 96 hours. T2 weighted whole body coronal (FIG. 9A) and axial (FIG. 9B) MRI showed an increase in T2 contrast in liver (shown in white dotted box) within the first one hour which gradually reduced to initial contrast by 96 hours. This variation was also reflected in the T2 relaxation values that drastically reduced in the first hour after injection beyond which it gradually increased to initial value in ~96 hours (FIG. 9C). This was due to the initial RES mediated accumulation of Fe-nCX within liver that gradually got metabolized or cleared over a period of 96 hours. This was confirmed by ICP analysis which showed that 1 hour after the sample injection, there was an increase in Fe3+ content in all organs as well as plasma with significantly higher concentration in the heart, plasma and liver (FIG. 9D). These results suggest that the nanoparticles circulated throughout the body for ~1-2 hours during which it slowly accumulated in the liver before being cleared or metabolized through hepatobiliary route.

Figure 10A:
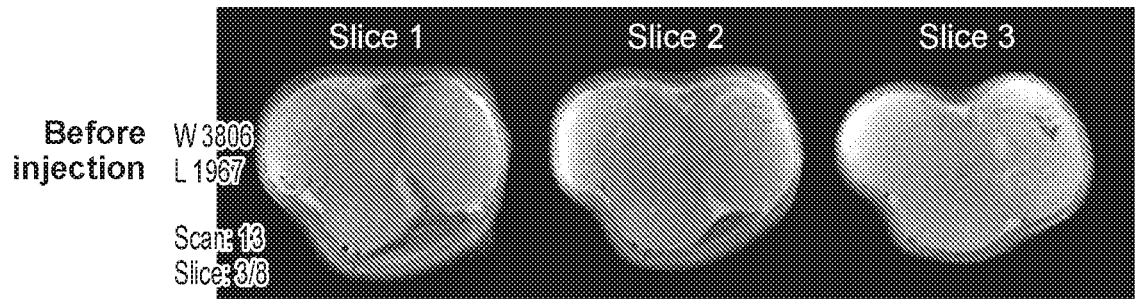
Figure 10B:
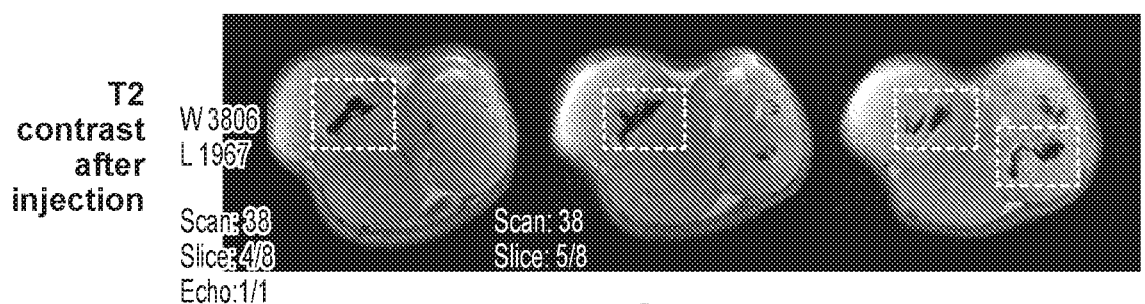
FIG. 10B shows T2 weighted and FIG. 10C shows T1 weighted MR image of subcutaneous tumour after intratumoral Fe-nCX (X=phosphate) injection.
Figure 10C:
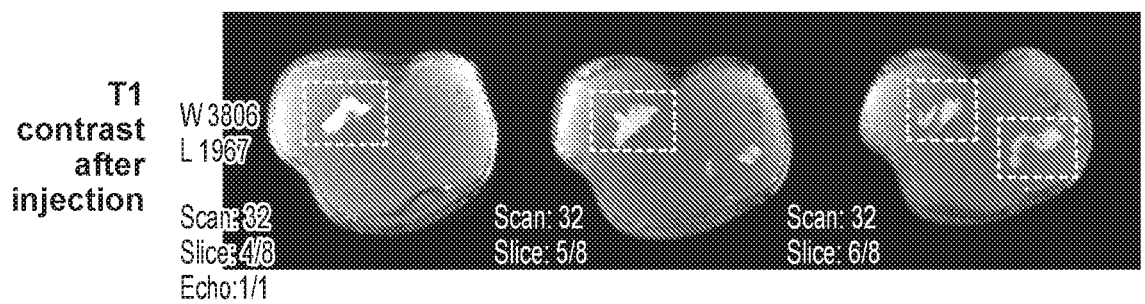

To test the ability of Fe-nCX to provide dual T1-T2 contrast on intra-tumoral injection, 10 mg/kg of sample was injected to subcutaneous tumor (C6 glioma) in Wistar rat. Excellent T2 and T1 contrast was observed from the sample injected regions (shown in white box: FIG. 10A-10C)

Example 3: In Vitro Radiofrequency Response of Fe-nCX (X=Phosphate)

Figure 11:
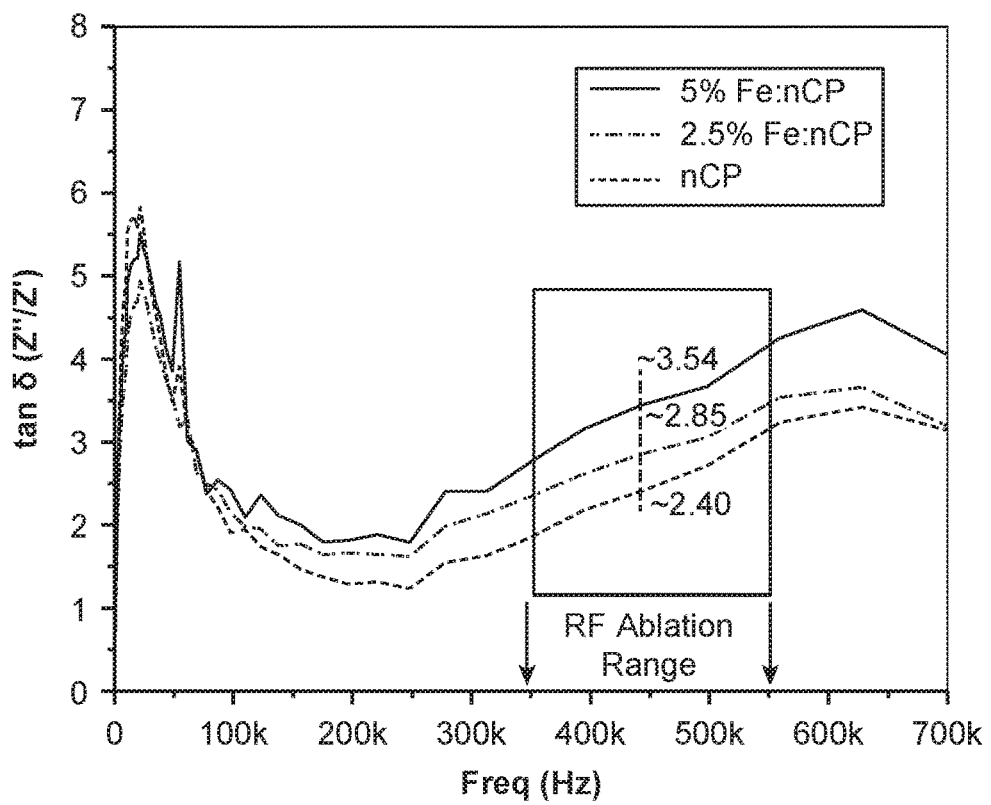
FIG. 11 shows impedance spectroscopy results illustrating radio wave responsiveness of doped nanoparticles.
Figure 12:
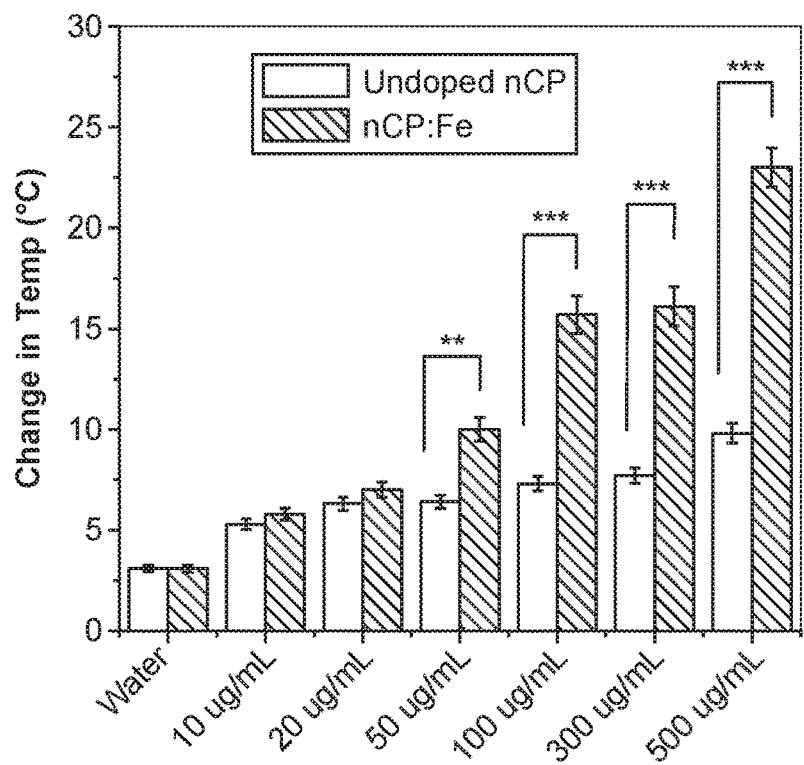
FIG. 12 depicts radiofrequency assisted heating of nanoparticles Fe-nCX (X=phosphate) at concentrations varying from 10-500 μg/ml at 100 W RF power for 1 minute.

RF response of the nanoparticles was measured in a custom made non-invasive 13.5 MHz RF instrument. Different concentrations of Fe-nCX varying from 10-500 µg/mL were taken in a small glass petri dish and 100 W RF power was applied for 1 minute. The temperature of the solution was measured before and after RF irradiation. In the frequency range applied for RF ablation (350-550 kHz), there was an increase in dielectric loss factor, tan delta value, from 2.4 for undoped nCP to 3.54 for Fe-nCX (FIG. 11), that indicates lossy character of doped sample under RF exposure. We compared the RF mediated heating of nCP and Fe-nCX at varying concentration at 100 W RF power for 1 minute exposure in a non-invasive RF machine. In the concentration range of 50-500 µg/mL, there was significant increase in temperature of up to 22° C. for Fe-nCX samples compared to only <10° C. for undoped nCP (FIG. 12). We presumed that this rise in temperature observed for Fe-nCX samples would be sufficient to enhance efficiency of RFA under in vivo conditions.

Figure 13A:
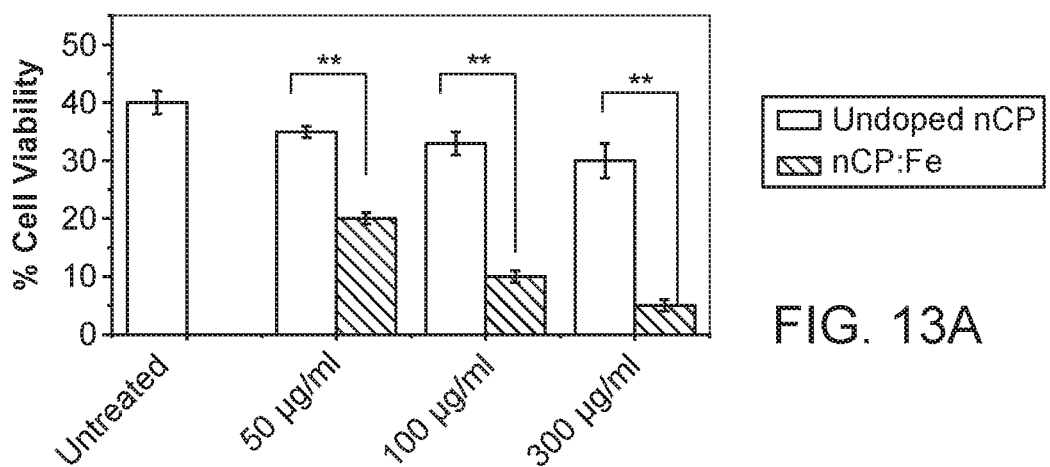
FIG. 13A shows RF response of C6 glioma cells treated with varying concentrations of Fe-nCX (X=phosphate) for 4 hours and FIG. 13B shows radio-wave responsive nanoparticles injected into rat liver tumor model with enhanced hyperthermal ablation (81.3° C.) compared to untreated animal (51.3° C.).
Figure 13B:
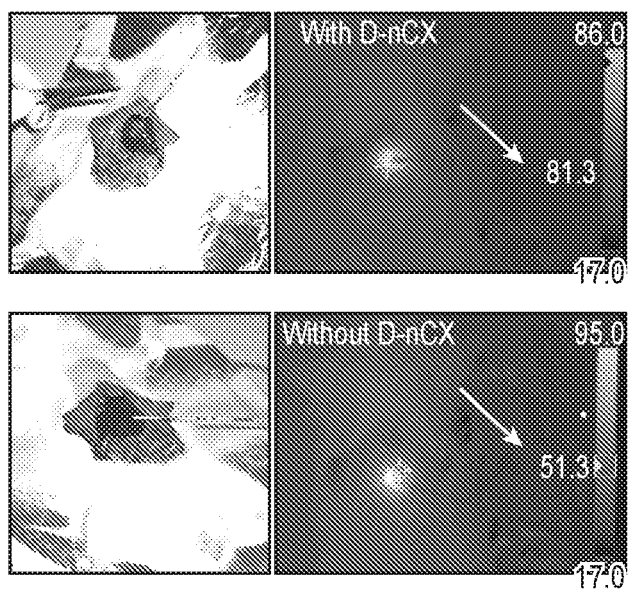

RF response of nanoparticle treated N1-S1 hepatoma cells was also tested using the same non-invasive RF instrument. N1-S1 cells were seeded in 24 well plates at a seeding density of $2.5 \times 10^4$ cells/well. Different concentrations of Fe-nCX (50-500 µg/mL) were added to the wells. After incubation with the nanoparticles for 4 hours, the cells are irradiated with 100 W RF power for 5 minutes. 4 hours after RF treatment, media was changed. After 48 hours, cell viability analysis was carried out using Alamar blue assay. There was a significant reduction in viability for cells treated with Fe-nCX compared to undoped nCP (FIG. 13A). In untreated control 40% of the cells were live after RF treatment. 300 µg/mL of undoped nCP reduced viability to ~31% whereas the same concentration of Fe-nCX reduced cell viability to 5%. This results were also repeated in animal models where we could see an increased temperature of 81 degree Celsius in D-nCP treated animal liver tumor (FIG. 13 B, top panel) compared to 51° C. in untreated animal (FIG. 13 B, lower panel).

Example 4: Method of Using D-nCX (X=Phosphate) Nanoparticles for Dual Mode MR or Dual Mode MR-CT Contrast Based Evaluation of Bone Tissue Regeneration—Preparation of Doped Calcium Phosphate-Alginate Beads with MR Contrast Iron Doped nCP Synthesis (Fe-nCX—X is Phosphate):
20 mL of 0.5 M calcium chloride ($CaCl_2$, Sigma, USA) was mixed with 20 mL of 0.2 M trisodium citrate ($Na_3C_6H_5O_7$, Fisher Scientific, India) and 0.1 M $FeCl_3$ (Sigma, USA). Volume of 0.1 M $FeCl_3$ added was varied as per the required percentage of doping. 5 mL of 0.3 M diammonium hydrogen phosphate (($NH_4)_2HPO_4$, S.D Fine Chemicals, India) mixed with 0.2 mL of 3 N ammonium hydroxide ($NH_4OH$, Fisher Scientific, India) was added drop wise to the above mixture of $CaCl_2$, $Na_3C_6H_5O_7$ and $FeCl_3$ under constant stirring to obtain Fe-nCX. The precipitate was washed 4 times in hot distilled water by centrifugation at 8500 rpm for 15 minutes and redispersed in PBS.

Preparation of Fe-nCX-Alginate Composite Beads:
10 mL of 3 wt % alginate solution was prepared and kept for stirring for 20 minutes until the alginate is completely solubilized. 60 wt % of Fe-nCX was added to the alginate solution and blended using mortar and pestle or a blender (IKA, US). The blended alginate-Fe-nCX was added drop wise to 1 wt % calcium chloride solution to form Fe-nCX-alginate beads. The beads were strained, washed thrice with distilled water and dried in hot air oven at 60° C. overnight.

Figures 14A, 14B:
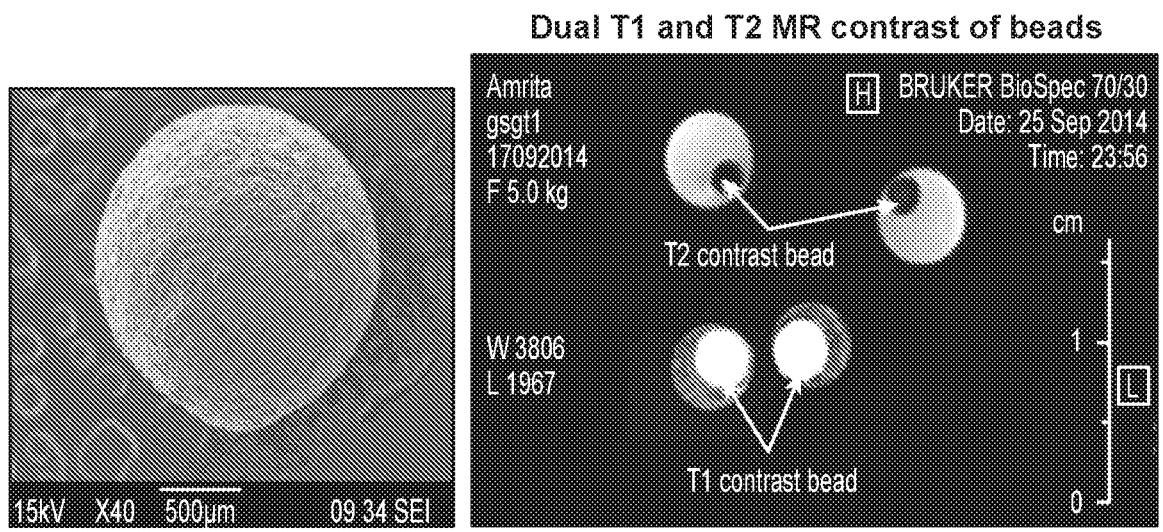
FIG. 14A is a photograph of undoped CP beads and FIG. 14B is SEM image of doped CP bead showing size ~1 μm (D) T1 and T2 weighted MRI of the Gd-nCX (X=phosphate) beads.
Figures 15A, 15B, 15C:
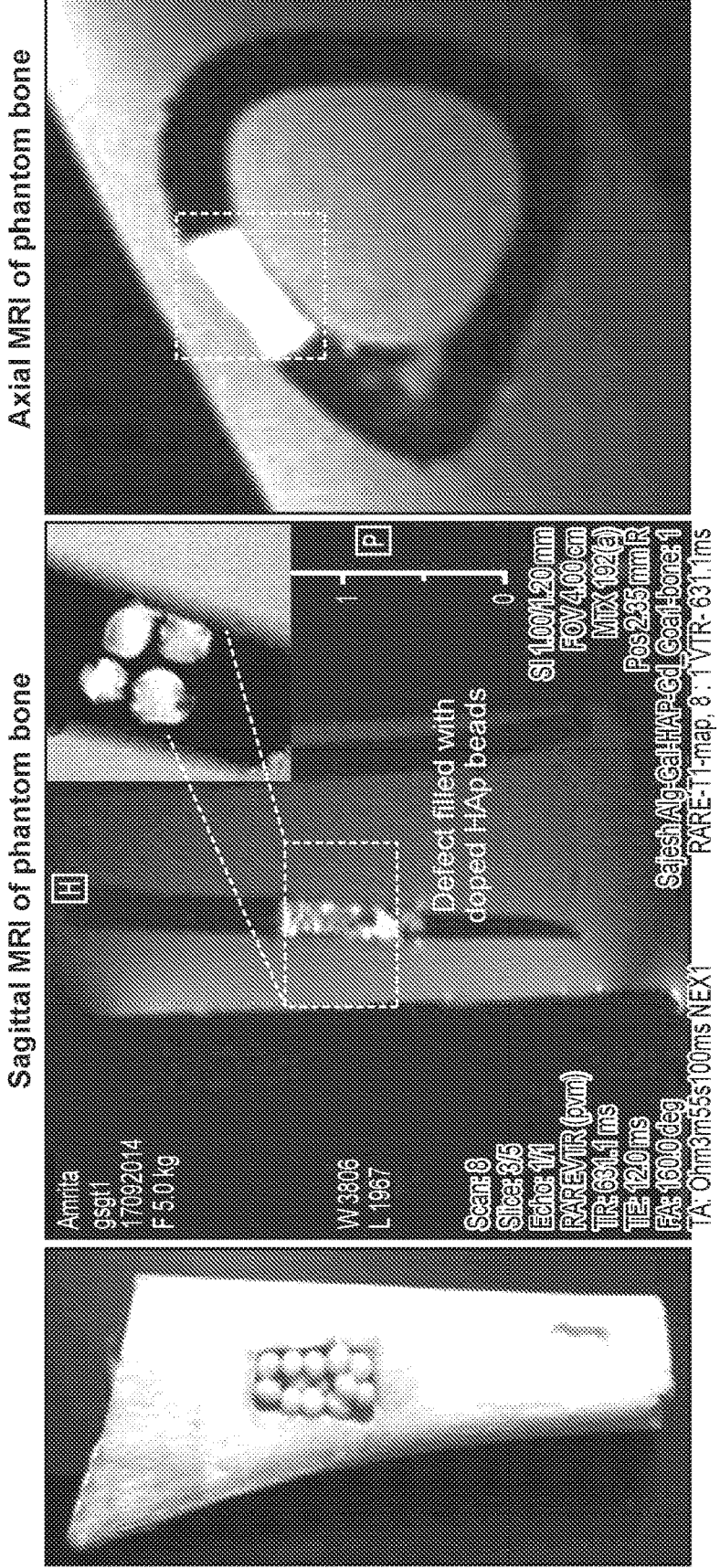
FIG. 15A is a photograph of phantom bone with small defect filled with Gd-nCX (X=phosphate)
FIG. 15B is T1 weighted MRI of the phantom bone defect filled with Gd-nCX beads, sagittal section.
FIG. 15C is axial T1 weighted MRI with bright T1 weighted contrast visible from Gd:nCX beads.

Characterization of Beads:
SEM image showed smooth surface morphology with size ~1 µm (FIG. 14A) T1 weighted and T2 weighted MRI of the beads showed dual contrast properties (FIG. 14B). The capability of Fe-nCX-alginate beads to provide contrast when placed in a bone defect was tested in a phantom bone sample (FIG. 15A). Defect of size ~1 cm was made in pig bone and filled with beads as shown in FIG. 15A. MRI showed bright T1 contrast from the beads (FIG. 15B, 15C).

Example 5: Doped Calcium Phosphate Nanoparticles for Image Guided Immunotherapy—Synthesis of Bisphosphonate (Zoledronic Acid) Loaded Doped Calcium Phosphate Nanoparticles for Activation of T Cells 20 mL of 0.5 M calcium chloride ($CaCl_2$, Sigma, USA) was mixed with 20 mL of 0.2 M trisodium citrate ($Na_3C_6H_5O_7$, Fisher Scientific, India) and 0.1 M FeCl (Sigma, USA). Volume of 0.1 M $FeCl_3$ added was varied as per the required percentage of doping. 5 mL of 0.3 M diammonium hydrogen phosphate (($NH_4)_2HPO_4$, S.D Fine Chemicals, India) mixed with 0.2 mL of 3 N ammonium hydroxide ($NH_4OH$, Fisher Scientific, India) was added drop wise to the above mixture of $CaCl_2$, $Na_3C_6H_5O_7$ and $FeCl_3$ under constant stirring to obtain Fe-nCX (X=phosphate). The precipitate was washed 4 times in hot distilled water by centrifugation at 8500 rpm for 15 minutes and redispersed in PBS. Zoledronic acid (1 mg/mL) was added to Fe-nCX solution and incubated at room temperature (22-37° C.) for 30 minutes. The zoledronic acid loaded Fe-nCX was then washed twice with distilled water to obtain the final product.

Example 6: CT and Nuclear Contrast of Radio-Sensitive Nanoparticles

Synthesis of Molybdenum Doped Calcium Phosphate Nanoparticles (Mo-nCX, X is Phosphate) and Demonstration of CT Contrast Property:

15 ml of 0.5M calcium chloride ($CaCl_2$, Sigma, USA) was mixed with 0.1M ammonium molybdate (($NH_4)_6Mo_7O_{24}.4H_2O$, Nice Chemicals, India). Volume of ammonium molybdate was varied according to the required percentage of doping. 5 ml of 0.3M diammonium hydrogen phosphate (($NH_4)_2HPO_4$, S.D Fine Chemicals, India) was mixed with 3N ammonium hydroxide ($NH_4OH$, Fisher Scientific, India) and added drop-wise to the reaction mixture, under constant stirring. Precipitate washed 5 times with distilled water and centrifugation at 7000 rpm for 10 minutes.

The CT contrast of the nanoparticles was assessed using the GE Hawkeye SPECT-CT system (GE Healthcare, USA). The contrast/attenuation provided by the nanoparticles was quantified with Hounsfield units (HU). The highest HU was obtained with 50% molybdenum doping.

Figure 16A:
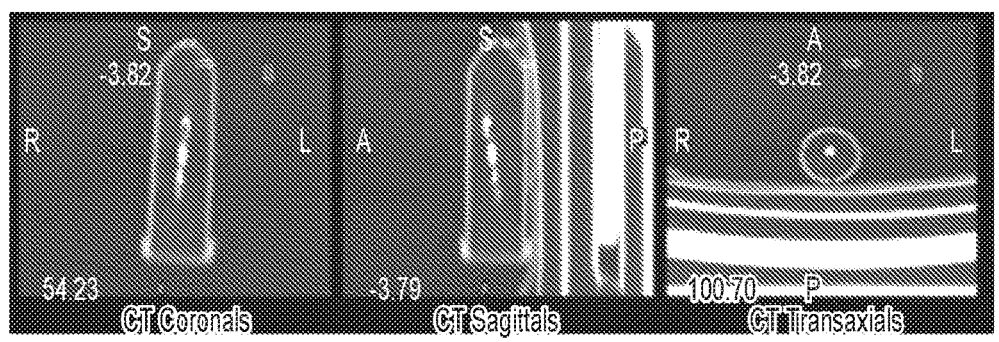
FIG. 16A shows coronal, sagittal and transaxial images using CT contrast.
Figure 16B:
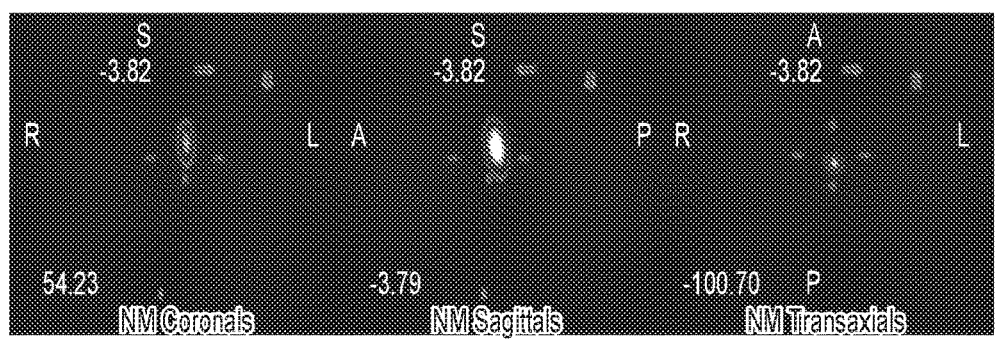
FIG. 16B shows nuclear contrast of the Mo-nCX (X=phosphate) microbeads in a cotton phantom and FIG. 16C shows fused CT-nuclear images confirming the findings.
Figure 16C:
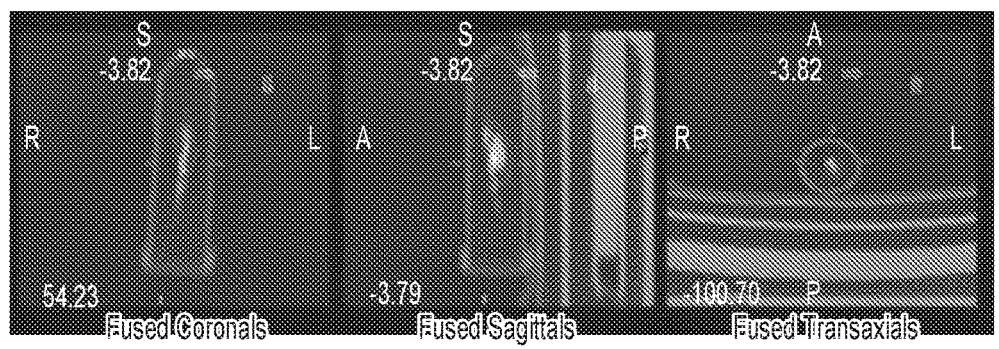
Figure 16D:
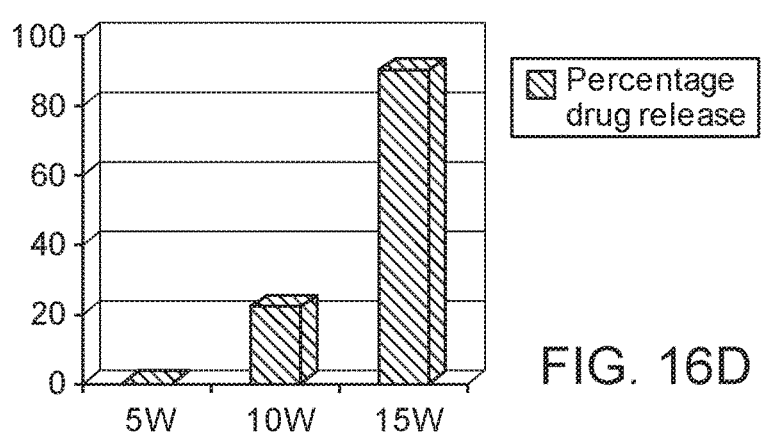
FIG. 16D shows drug release data at different RF power applied of doxorubicin incorporated into Mo-nCX beads.

Method of Combined CT and Nuclear Contrast Property of Microbeads Made of Molybdenum Doped Calcium Phosphate Nanoparticles:

1% sodium alginate (Sigma, USA) solution was prepared and under constant stirring the molybdenum doped calcium phosphate nanoparticles (80% w/w of sodium alginate) was slowly added slowly and kept for stirring at room temperature for 2 hours. Using a micro pipette, this alginate-nanoparticle mixture was dropped into 2% (w/v) calcium chloride (Fisher Scientific, India) solution to produce the microbeads. The beads were removed after 2 hours form the $CaCl_2$ solution, washed 5 times with distilled water and dried for 24 hours in a hot-air oven (60° C.). 30 mCi of 99m Technetium Methylene Diphosphonate (tracer) was added to 50 mg of the microbeads and incubated at room temp for 2 hours. The excess untagged tracer was washed using distilled water. FIG. 16A, depicts the CT contrast offered by the beads which were placed in a cotton phantom. FIG. 16B shows the corresponding nuclear contrast from the same beads. The same GE imaging system was used for the evaluation. The fused hybrid images (nuclear and CT) in FIG. 16C confirm the beads to simultaneously have both CT and nuclear contrast. After application of RF of different power, the doxorubicin loaded microbeads shows controlled drug release. (FIG. 16D).

Example 7: Method of RF Triggered Drug Release from Microbeads Prepared Using RF Responsive Calcium Phosphate Coloaded with Doxorubicin 1% sodium alginate (Sigma, USA) solution was prepared. Under constant stirring the Mo-nCX (X is phosphate) (80% w/w of sodium alginate) and Doxorubicin (Dox) (0.5% w/w of sodium alginate) were slowly added slowly and kept for stirring at room temperature for 2 hours. Using a micro pipette, this mixture was dropped into 2% (w/v) calcium chloride (Fisher scientific, India) solution to produce the microbeads. The beads were removed after 2 hours form the $CaCl_2$ solution, washed 5 times with distilled water and dried for 24 hours in a hot-air oven (60° C.). To study the drug release, multiple samples of 5 mg of the dried beads suspended in 25 ml of phosphate buffered saline were prepared and maintained at 37° C. Each of the samples was exposed to uniform RF (13.56 MHz) field of 5 W, 10 W and 15 W power for 1 minute, and the drug released into PBS immediately after exposure was measured using a UV spectrometer, at 488 nm (FIG. 16 D).

Example 8: Method of Labelling Stem Cells with Fe-nCX (X=Phosphate) and its MR Guided Tracking in Brain Fe-nCX was used for labelling rat mesenchymal stem cells (rMSC) and tracking stem cell migration after injection to rat brain. rMSC were isolated from rat femur bone marrow. The effect of nanoparticle tagging on the proliferation of rMSC was investigated for a period up to 7 days. It was observed that there was no change in proliferation of labelled cells compared to unlabelled rMSC (FIG. 17A). This confirmed that the nanoparticles do not affect the proliferative capability of the stem cells. 100 µg/mL of Fe-nCX was treated with these cells for a period of 12 hours. FIG. 17B shows the Prussian blue stained nanoparticle within rMSc after incubation for period of 12 hours. For MRI of cell pellet, 100 µg/mL of Fe-nCX was treated with these cells for a period of 12 hours. The untagged nanoparticles were washed with PBS, trypsinised and centrifuged to form pellet. MRI of the labelled cell pellet showed T2 based dark contrast compared to unlabelled cells (FIG. 17C). T2 value of unlabelled cell pellet was 121 mS and that of labelled cells was 67 mS. The reduction in T2 value clearly shows the T2 shortening effect of Fe-nCX. $10^5$ Fe-nCX labelled rMSC were injected into the rat brain and tracked upto a period of 7 days. MRI of the rat brain clearly showed the injected cells (FIG. 17E) compared to control brain injected with unlabelled cells (FIG. 17D).

Figure 18:
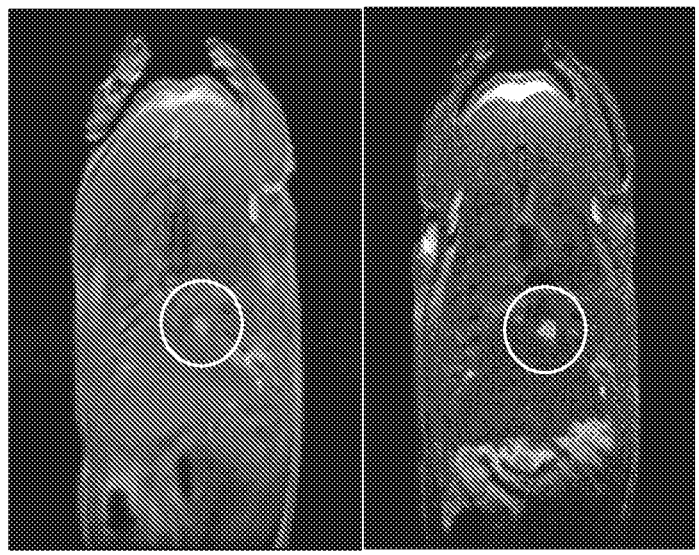
FIG. 18 is MRI of coronal section of orthotopic rat liver tumor model before sample injection (left) and after Fe-nCX (X=phosphate) injection (right), showing tumor margins more clearly demarcated after injection.

Example 9: Method of Using the Fe-nCX (X=Phosphate) Nanoparticles for Cancer Detection Fe-nCX was used for the identification of small liver tumor in orthotopic rat liver tumor model. 10 mg/kg of the nanoparticles was injected to orthotopic rat liver tumor model and MRI was carried out after 10 minutes. As seen in FIG. 18, the small liver tumor margin was clearly demarcated after Fe-nCX injection (FIG. 15B). This is due to the accumulation of the nanoparticles in the normal liver region (uptake by kupffer cells in healthy liver region) that enhances the relative contrast of the tumor.

Figure 19A:
FIG. 19A is MRI of cells growing in Fe-nCX (X=phosphate) scaffold seen as white spots growing through the Fe-nCX incorporated scaffold.
Figure 19B:
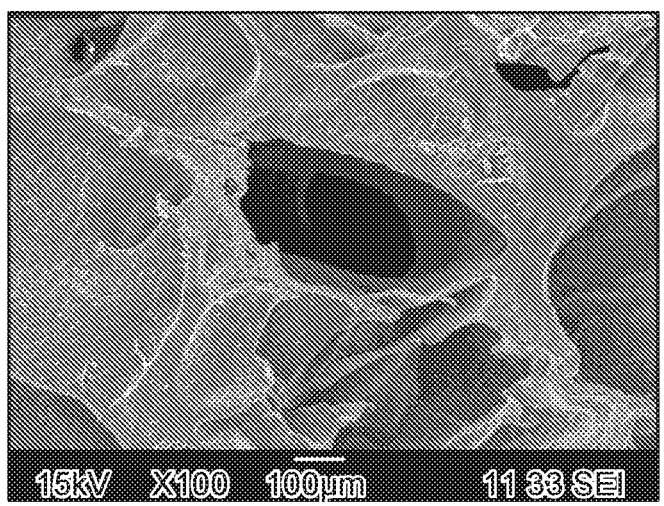
FIG. 19B is SEM image of Fe-nCX incorporated scaffold and FIG. 19C is SEM image of cells growing on Fe-nCX scaffold.
Figure 19C:
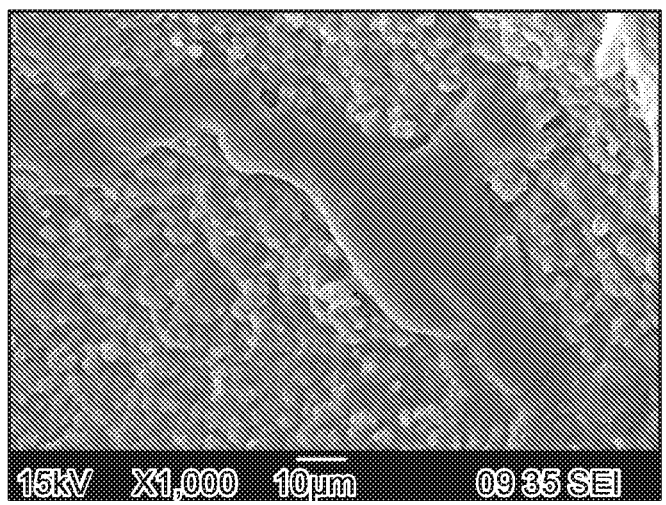

Example 10. Method of Using Fe-nCX (X=Phosphate) Nanoparticles Containing Scaffold for Tissue Regeneration Fe-nCX scaffold provides an enhanced T2 contrast compared to undoped scaffold due to the T2 shortening by $Fe^{3+}$ions. Cell ingrowth and tissue regeneration into the scaffold can be evaluated using MRI. As shown in FIG. 19A, the white spots seen in the Fe-nCX scaffold are cells growing into the scaffold. The undoped scaffold shows a bright contrast and the cells cannot be spotted in the undoped scaffold. FIG. 19B shows SEM image of the scaffold showing its macro porous nature facilitating cell growth and proliferation. FIG. 19C shows mesenchymal stem cell growing on the scaffold. The morphology of the attached cells showed that the scaffold is compatible to the mesenchymal stem cells.

Example 11: Delivery D-nCX to Immune Cells to Stimulate or Cytokine Release

In this example we showed that the said nanoparticles can be delivered to immune cells like macrophages in large concentrations as shown in FIGS. 20A and 20B. The spherical particles are D-nCX taken up by the macrophages. This delivery caused release of pro-inflammatory cytokines from the immune cells (macrophages) as shown in the flow cytometry data (FIG. 20 C (Before treatment) and FIG. 20 D (after treatment).

What is claimed is:

1. A radio-wave responsive particle formulation, comprising:
   a doped anion-cation complex represented as D-C X, wherein:
   C is calcium cation ($Ca^{2+}$);
   X is an anion selected from the group consisting of phosphate, pyrophosphate, and phosphosilicate; and
   D is a dopant comprising 0.0001 to 50 atomic % of Mo and 1.5 to 6 atomic % of Fe, relative to $Ca^{2+}$;
   wherein the complex is configured to:
      generate heat under exposure to radiofrequency (RF) waves;
      provide simultaneous T1 and T2 contrast under magnetic resonance imaging (MRI); and
      provide X ray contrast under CT imaging,
   wherein the particle formulation comprises particles that are nano- or micro-particles having a size in a range of 1-2000 nm.

2. The particle formulation of claim 1, wherein the doped anion-cation complex is further configured to:
   provide near infrared fluorescence for optical imaging; or
   provide nuclear contrast for medical imaging.

3. The particle formulation of claim 2, wherein the complex is configured to:
   provide near infrared fluorescence emission at a 650-1000 nm spectral region, by doping (D) with an organic molecule selected from the group consisting of indocyanine green and fluorescein, at levels from 0.0001 to 50 weight % of the complex; or
   provide nuclear contrast for one or more of single photon emission computed tomography, positron emission tomography (SPECT/PET), or radionuclide mediated therapy by surface labelling with a radionuclide selected from the group consisting of $^{153}$Sm, $^{99}$mTc, $^{123}$I, $^{111}$In, $^{188}$Re, $^{166}$Ho, $^{90}$Y, $^{82}$Rb, $^{225}$Ac, $^{211}$At, $^{212}$Bi, $^{223}$Ra, $^{212}$Pb, $^{227}$Th, and $^{149}$Tb.

4. The particle formulation of claim 1, wherein the calcium cation of the doped anion-cation complex is derived from a compound selected from the group consisting of beta-tricalcium phosphate ($Ca_3(PO_4)_2$), calcium dihydrogen phosphate ($Ca(H_2PO_4)_2$), calcium hydrogen phosphate (CaHPO4), monocalcium phosphate monohydrate ($Ca(H_2PO_4) \cdot H_2O$), dicalcium phosphate dihydrate ($CaHPO_4 \cdot 2H_2O$), tetracalcium phosphate ($Ca_4(PO_4)_2O$), octacalcium phosphate ($Ca_8H_2PO_4)_6 \cdot 5H_2O$), fluoroapatite ($Ca_5(PO_4)_3F$), chlorapatite ($Ca_5(PO_4)_3Cl$), and a calcium phosphosilicate comprising 35-65 wt % of $SiO_2$, 1-50 wt % of $Na_2O$, 10-90 wt % of CaO, and 1-50 wt % of $P_2O_5$, and combinations thereof.

5. The particle formulation of claim 1, wherein the heat generated is up to 100° C. on exposure to a radiofrequency field of a frequency ranging from 1 Hz to 100 GHz and power in a range 1 to 1000 W for a time period ranging from 0.1 second to 1 hour.

6. The particle formulation of claim 5, wherein the heat generated is up to 100° C. on exposure to the radiofrequency field of a frequency of 314 kHz and the power of 100 W for the time period of 1 hour.

7. The particle formulation of claim 1, wherein the formulation is selected from one of $(CaFe_xMo_y)_3(PO_4)_2$, $(CaFe_xMo_y)_{10}(PO_4)_6(OH)_2$, or $(CaFe_xMo_y)NaO_6PSiO_4$, where x for Fe varies from 1.5 to 6 atomic % relative to $Ca^{2+}$, and y for Mo varies from 0.0001 to 50 atomic % relative to $Ca^{2+}$.

8. The particle formulation of claim 1, wherein the particles have a spherical shape.

9. The particle formulation of claim 8, wherein the particles have an average size in a range of 150 ±100 nm.

10. The particle formulation of claim 1, further loaded with therapeutic agents for radio-wave-triggered controlled drug release.

11. A radio-wave responsive micro-bead formulation, comprising:
    a doped anion-cation complex represented as D-C X, wherein:
    C is calcium cation ($Ca^{2+}$);
    X is an anion selected from the group consisting of phosphate, pyrophosphate, and phosphosilicate; and
    D is a dopant comprising 0.0001 to 50 atomic % of Mo and 1.5 to 6 atomic % of Fe, relative to $Ca^{2+}$;
    wherein the complex is configured to:
       generate heat under exposure to radiofrequency (RF) waves;
       provide simultaneous T1 and T2 contrast under magnetic resonance imaging (MRI); and
       provide X ray contrast under CT imaging, wherein
    the micro-bead formulation is selected from one or more formulations selected from the group consisting of:
    a radio-wave responsive, MR, CT, nuclear and/or NIR imageable micro-bead formulation ranging in size from 1 μm to 1 mm for vascular embolization or tissue implantation;
    a radio-wave responsive, MR, CT, nuclear and/or NIR imageable micro-bead formulation labelled with radioisotopes for radio-embolization therapy; and
    a radio-wave responsive, MR, CT, nuclear and/or NIR imageable formulation for culturing, proliferating, differentiating, activating, or reprogramming biological cells for therapeutics.

12. The micro-bead formulation of claim 11, wherein the formulation is a radio-wave responsive, MR-CT contrast enabled, and micro-beads in the micro-bead formulation have a size in a range of 200 ±100 μm, for embolization or tissue implantation.

* * * * *